(12) United States Patent
Oetter et al.

(10) Patent No.: US 9,212,545 B2
(45) Date of Patent: Dec. 15, 2015

(54) USE OF TRIS(2-HYDROXYPHENYL)METHANE DERIVATIVES FOR TERTIARY MINERAL OIL PRODUCTION

(71) Applicant: Wintershall Holding GmbH, Kassel (DE)

(72) Inventors: Günter Oetter, Frankenthal (DE); Björn Heinz, Mannheim (DE); Markus Hansch, Speyer (DE); Horst Weiss, Neuhofen (DE); Peter Deglmann, Mannheim (DE); Vandana Kurkal-Siebert, Heidelberg (DE); Frank Heilmann, Dirmstein (DE); Ravindra Aglave, Katy, TX (US); Lorenz Siggel, Heidelberg (DE); Benjamin Wenzke, Hamburg (DE)

(73) Assignee: Wintershall Holding GmbH, Kassel (DE)

( * ) Notice: Subject to any disclaimer, the term of this patent is extended or adjusted under 35 U.S.C. 154(b) by 397 days.

(21) Appl. No.: 13/653,946

(22) Filed: Oct. 17, 2012

(65) Prior Publication Data
US 2013/0098609 A1 Apr. 25, 2013

Related U.S. Application Data

(60) Provisional application No. 61/550,465, filed on Oct. 24, 2011.

(30) Foreign Application Priority Data

Oct. 18, 2011 (EP) ...................................... 11185626

(51) Int. Cl.
*E21B 43/16* (2006.01)
*C07C 41/03* (2006.01)
(Continued)

(52) U.S. Cl.
CPC ................. *E21B 43/16* (2013.01); *C07C 39/10* (2013.01); *C07C 41/03* (2013.01); *C08G 65/2612* (2013.01); *C08G 65/3344* (2013.01); *C09K 8/584* (2013.01); *C09K 2208/30* (2013.01)

(58) Field of Classification Search
CPC ........ C09K 8/68; C09K 2208/32; C09K 3/00; C09K 3/30; C09K 5/045; C09K 5/048; C09K 8/00; C09K 8/04; C09K 8/22; C09K 8/52; C09K 8/54; C09K 8/58; C09K 8/584; C09K 8/605; C09K 8/805; E21B 33/068; E21B 33/1204; E21B 33/1208; E21B 33/127; E21B 33/1285; E21B 34/00; E21B 34/066; E21B 34/08; E21B 34/12; E21B 36/00; E21B 36/008; E21B 3/00; E21B 41/0085; E21B 43/082; E21B 34/10; E21B 43/08; E21B 34/14; E21B 41/00; E21B 47/12; E21B 19/08; E21B 34/02; E21B 34/16; E21B 43/16; E21B 43/164; E21B 47/06;

E21B 7/12; E21B 10/42; E21B 10/43; E21B 10/5735
See application file for complete search history.

(56) References Cited

U.S. PATENT DOCUMENTS 5,668,227 A 9/1997 Wolleb et al.
5,741,947 A 4/1998 Wolf et al.
(Continued)

FOREIGN PATENT DOCUMENTS

DE 4325237 A1 2/1995
DE 10243361 A1 4/2004
(Continued)

OTHER PUBLICATIONS

"Petroleum, Enhanced Oil Recovery" Kirk-Othmer Encyclopedia of Chemical Technology, Wiley (2005) vol. 18, pp. 1-29.
(Continued)

*Primary Examiner* — Susannah Chung
*Assistant Examiner* — Kumar R Bhushan
(74) *Attorney, Agent, or Firm* — Drinker Biddle & Reath LLP

(57) ABSTRACT

A process for mineral oil production, in which an aqueous formulation comprising tris(2-hydroxyphenyl)methane of the general formula (I) is injected into a mineral oil deposit through an injection well and the crude oil is withdrawn from the deposit through a production well,

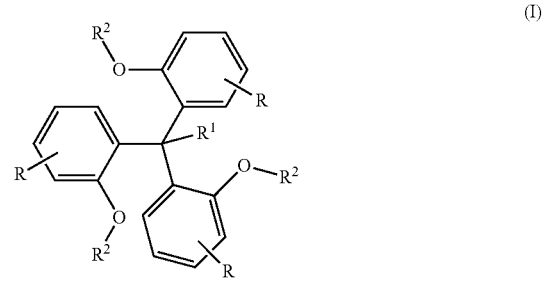

where the $R^1$, $R^2$ and R radicals in the formula (I) are each defined as follows:
R is independently 1 to 2 hydrocarbyl radicals per phenyl ring,
$R^1$ is preferably H or OH,
$R^2$ are independently radicals of the general formula (III), $$—(R^5—O—)_n—R^6—X \qquad (III)$$

Figure 1:
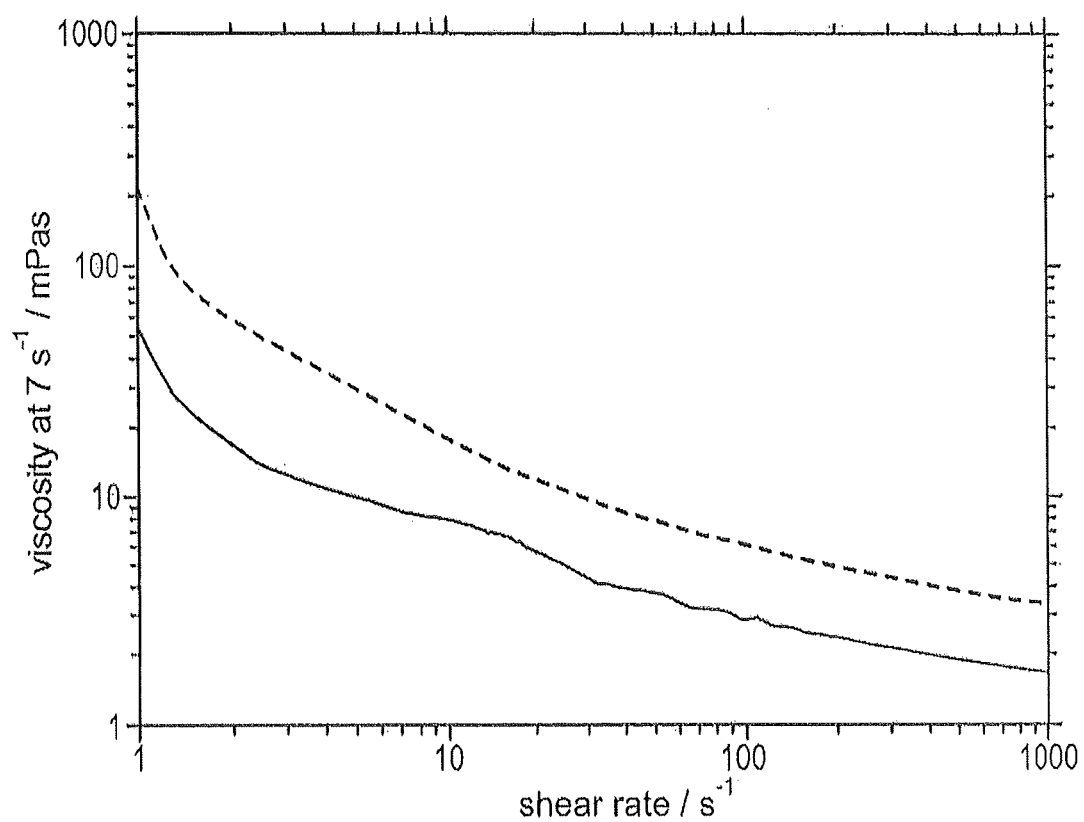

where n is a number from 1-50, and where the $R^5$ radicals are $R^7$ groups

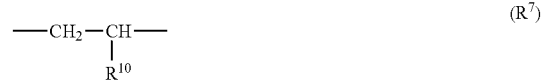

$R^6$ is a single bond or an alkylene group having 1 to 10 carbon atoms,
X is H or an acidic end group,
$R^{10}$ is, for example, $C_1$-$C_6$-hydrocarbyl radical, enables improved mineral oil production.

17 Claims, 6 Drawing Sheets

(51) Int. Cl.
  *C09K 8/584* (2006.01)
  *C07C 39/10* (2006.01)
  *C08G 65/26* (2006.01)
  *C08G 65/334* (2006.01)

(56) References Cited

U.S. PATENT DOCUMENTS

| | | | |
|---|---|---|---|
| 7,053,127 | B1 | 5/2006 | Treybig et al. |
| 7,373,977 | B1 | 5/2008 | Berger et al. |
| 7,461,694 | B2 | 12/2008 | Dahanayake et al. |
| 2004/0214725 | A1 | 10/2004 | Moss |
| 2005/0155762 | A1 | 7/2005 | Chen et al. |
| 2005/0170991 | A1 | 8/2005 | Ruland et al. |
| 2006/0084579 | A1 | 4/2006 | Berger et al. |
| 2006/0105919 | A1 | 5/2006 | Colaco et al. |
| 2006/0183646 | A1 | 8/2006 | Welton et al. |
| 2007/0107897 | A1 | 5/2007 | Dahanayake et al. |
| 2009/0056942 | A1 | 3/2009 | Dahanayake et al. |
| 2009/0155714 | A1 | 6/2009 | Lee et al. |
| 2009/0291864 | A1 | 11/2009 | Hartshorne et al. |
| 2011/0288322 | A1* | 11/2011 | Garcia et al. ............ 558/23 |

FOREIGN PATENT DOCUMENTS

| | | |
|---|---|---|
| EP | 0597806 B1 | 1/1998 |
| EP | 1 707 561 A1 | 10/2006 |
| GB | 2408506 B | 6/2007 |
| WO | WO-2008100436 A1 | 8/2008 |
| WO | WO-2011/144643 A1 | 11/2011 |

OTHER PUBLICATIONS

Ezrahi, et al. "Properties, main applications and perspectives of worm micelles" Advances in Colloid and Interface Science (2006) pp. 77-102.

Keli, et al. "Expanding Applications for Viscoelastic Surfactants" Oilfield Review, vol. 16(4), (2004) pp. 10-23.

Kessel, "Chemical Flooding—Status Report" Journal of Petroleum Science and Engineering, 2 (1989) pp. 81-101.

Shvets, et al., "Stabilization of Finely Dispersed Suspensions of Water-Insoluble Organic Dyes by Nonionic Surfactants" J.of Applied Chem. of USSR (1985) pp. 1220-1224.

Chen, X., et al., "Micellization of and Solute Binding to Amphiphilic Poly(ethylene oxide) Star Polymers in Aqueous Media", Langmuir, vol. 12, (1996), pp. 2207-2213.

Geczy, I., et al., "Surface Active Properties and Possibilities of Technological Application of Non-Ionic Addition Products of Polyoxiethylated Fatty Alcohols with Isocyanates", Kolorisztikai Ertesito, vol. 24, No. 3, (1983), pp. 142-147.

International Search Report for PCT/EP2012/070245 dated Jan. 22, 2013.

* cited by examiner

USE OF TRIS(2-HYDROXYPHENYL)METHANE DERIVATIVES FOR TERTIARY MINERAL OIL PRODUCTION

CROSS-REFERENCE TO RELATED APPLICATIONS

This application claims the benefit of European Application No. 11185626.6, filed Oct. 18, 2011, and U.S. Provisional Application 61/550,465, filed Oct. 24, 2011, which are incorporated herein by reference.

The present invention relates to the use of tris(2-hydroxyphenyl)methane derivatives for tertiary mineral oil production. The invention also provides a process for mineral oil production, in which an aqueous formulation comprising at least one tris(2-hydroxyphenyl)-methane derivative is used, the latter being injected into a mineral oil deposit through at least one injection well, for example with a deposit temperature of 10° C. to 150° C., and the crude oil being withdrawn from the deposit through at least one production well.

In natural mineral oil deposits, mineral oil is often present in the cavities of porous reservoir rocks which are sealed toward the surface of the earth by impervious overlying strata. The cavities may be very fine cavities, capillaries or pores. Fine pore necks may, for example, have a diameter of only approx. 1 μm. As well as mineral oil and proportions of natural gas, the deposits often also comprise salt-containing water. More particularly, the use of assistants for mineral oil production from salt-rich rock formations may be difficult.

In mineral oil production, a distinction is made between primary, secondary and tertiary production. In primary production, the mineral oil flows, after commencement of drilling of the deposit, of its own accord through the borehole to the surface due to the autogenous pressure of the deposit. The autogenous pressure results from the load on the essentially water-filled overlying rock strata. However, the autogenous deposit pressure often declines rapidly in the course of withdrawal of mineral oil, and so it is usually possible to produce only approx. 5 to 10% of the amount of mineral oil present in the deposit by means of primary production, according to the deposit. Thereafter, the autogenous pressure is no longer sufficient for production of mineral oil, and so pumps are often used thereafter for further mineral oil production.

After primary production, secondary production can therefore be used, in which, in addition to the boreholes which serve for production of the mineral oil, called the production wells, further boreholes are drilled into the mineral oil-bearing formation. These are called injection wells and are used to inject water into the deposit (called "water flooding"), in order to maintain the pressure or increase it again.

As a result of the injection of water or of a corresponding aqueous formulation, the mineral oil is also forced gradually through the cavities in the formation, preceding from the injection well in the direction of the production well. However, this only works for as long as the relatively high-viscosity oil is pushed onward by the water. As soon as the mobile water breaks through to the production wells along preferred flow paths, it flows on the path of least resistance from this time, i.e. particularly through the flow paths formed, and barely displaces any oil. By means of primary and secondary production, generally only approx. 30 to 35% of the amount of mineral oil present in the deposit can be produced.

After the measures of secondary mineral oil production (or after measures of primary mineral oil production), measures for tertiary mineral oil production (also known as "enhanced oil recovery", EOR) are also used to further enhance the oil yield. These include processes in which suitable chemicals, such as surfactants and/or polymers, are used as assistants in formulations for oil production. An overview of tertiary oil production using chemicals can be found, for example, in an article by D. G. Kessel from 1989 (Journal of Petroleum Science and Engineering, 2 (1989), 81 to 101).

One of the known techniques for tertiary mineral oil production is that known as "polymer flooding", in which an aqueous solution of a thickening polymer is injected into the mineral oil deposit through the injection wells, the viscosity of the aqueous polymer solution being matched to the viscosity of the mineral oil. Instead of a polymer solution, it is also possible to use aqueous solutions comprising nonpolymeric thickeners.

Thickeners are chemicals which increase the viscosity of aqueous solutions, extending as far as gel formation. The injection of a thickened solution forces the mineral oil through the cavities in the formation preceding from the injection well in the direction of the production well, and allows the mineral oil to be produced through the production well. The fact that a thickener formulation has about the same mobility as the mineral oil reduces the risk that the formulation breaks through to the production well without having any effect ("fingering").

Thus, it is possible with thickener to mobilize the mineral oil much more homogeneously and efficiently than in the case of use of mobile water, by avoiding the occurrence of "fingering" in the case of use of water. Furthermore, piston-like displacement of the oil is achieved by the matching of the mobility. This accelerates the production of the mobile oil with regard to water flooding.

In addition, in the case of tertiary mineral oil production, it is also possible to use surfactants in addition to thickeners. Surfactants are used in mineral oil production in order to lower the oil-water interfacial tension to very low values and thus to mobilize further mineral oil which would otherwise remain in the rock.

The subsequent injection of a thickened water solution forces the mineral oil thus mobilized, as in the case of water flooding, preceding from the injection well in the direction of the production well, thus allowing it to be produced through the production well. Details of flooding with thickened or surfactant-containing solutions and components suitable therefor are described, for example, in "Petroleum, Enhanced Oil Recovery" (Kirk-Othmer, Encyclopedia of Chemical Technology, John Wiley & Sons, 2005).

In some cases, such a combination of successive "surfactant flooding" and "polymer flooding" is preceded by a phase involving an alkaline agent such as sodium hydroxide solution, in order to mobilize natural surfactants present in the crude oil ("alkaline polymer-surfactant flooding"). For the aforementioned combination of successive "surfactant flooding" and "polymer flooding", it is also possible to use what are called viscoelastic surfactants. These viscoelastic surfactants are interface-active substances which, in solution, form associates which increase the viscosity of the solution.

For examples thereof, reference is made to "Molecular Gels: Materials with Self-Assembled Fibrillar Networks" (Richard G. Weiss, Pierre Terech, Dec. 22, 2005), Advances in Colliod and Interface Science 128-130 (2006) 77-102). With viscoelastic surfactants, it is possible to achieve a reduction in interfacial tension which cannot be achieved with polymeric components alone. Thickening surfactants for mineral oil production are described in various places. "Oilfield Reviews" (Vol. 16(4) (2004) 10-28) describes the use of viscoelastic surfactant systems as "fracturing fluids". As early as 1985, V. Shvets described the stabilization of suspensions by the use of nonionic surfactants (Journal of Applied Chemistry of USSR, 58 (6), 1985, 1220-1224).

The following documents US 2009/0056942, US 2007/0107897, US 2006/0183646, US 2006/0084579, US 2005/0155762, US 2009/291864, US 2006/105919, US 2004/214725, U.S. Pat. Nos. 7,461,694, 7,373,977, 7,053,127, and GB-A2,408,506 describe the use of viscoelastic surfactants for mineral oil applications, for example for tertiary mineral oil production.

The so-called associates that surfactants can form are also called micelles and form due to hydrophobic interactions.

The thickening properties of such solutions can generally be eliminated by shear, in which case the associates fall apart into smaller fragments. This operation, however, does not break any chemical bonds, and the associates develop their full thickening action again in the absence of shear.

This is an advantage of viscoelastic surfactant systems, more particularly over synthetic polymeric thickeners, which can be destroyed irreversibly by strong shear, for example in the course of pumping of a solution into an oil reservoir. An additional effect is the fact that viscoelastic surfactants lower the water-oil interfacial tension, which is the case only to a distinctly lesser degree, if at all, for polymers.

It is an object of the invention to provide a process for mineral oil production, which can be performed in an inexpensive and technically uncomplicated manner, and which can also be used in the case of salt-containing oil deposits. Especially in the case of high salt contents (for example at least 10 000 ppm, often at least 20 000 ppm, especially at least 50 000 ppm), it may be advantageous to use synthetic-based thickeners other than polymeric thickeners in tertiary mineral oil production.

The nonpolymeric derivatives of tris(2-hydroxyphenyl) methanes which are used in accordance with the invention and which have, as functional groups, unmodified polyalkoxy groups or polyalkoxy groups modified with terminal hydroxyl groups act as highly effective surfactants or thickeners, even at elevated temperatures and/or high salt content.

The compound tris(2-hydroxyphenyl)methane and various derivatives thereof have been known for years; for instance, G. Casiraghi (Tetrahedron Letters, No. 9, 679 to 682, 1973) describes the synthesis of mono- or dialkylated tris(2-hydroxyphenyl)methanes by reaction of appropriate phenols with triethyl orthoformates. M. B. Dinger and M. J. Scott (Chem. Commun., 1999, 2525-2526, Inorg. Chem. 2000, 39, 1238-1254 and Inorg. Chem. 2001, 40, 1029-1036) describe the synthesis of various tris(3,5-dialkyl-2-hydroxyphenyl)methane derivatives, the alkyl radicals described being methyl, t-butyl and t-pentyl radicals.

The trishydroxyphenylmethane compounds are used as complexing agents for zinc and alkali metal ions. M. B. Dinger and M. J. Scott, (Eur J. Org. Chem. 2000, 2467 to 2478) also describe the further conversion of the OH group of tris(3,5-dialkyl-2-hydroxyphenyl)-methanes.

The OH functions can be derivatized by reaction with halocarboxylic esters and hydrolysis and/or further conversions. M. B. Dinger and Scott describe, for example, tris(3,5-di-t-butyl-2-carboxymethoxyphenyl)methane, tris(3,5-di-tert-butyl-2-[(dimethylamido)methoxy]-phenyl)methane, tris{3,5-di-tert-butyl-2-[N-(methylglycyl)carbonylmethoxy] phenyl}methane and tris(3,5-di-tert-butyl-2-[(benzylaminocarbonyl)methoxy]phenyl)methane. The derivatives can each be used as complexing agents, for example for Zn(II) ions.

The authors K. Matloka (Dalton Trans., 2005, 3719 to 3721 or Separation Science and Technology, 41, 2006, 2129 to 2146) and M. W. Peters (Inorg. Chem., 2002, 41, 1701 to 1716) disclose functionalized tris(3,5-dialkyl-2-hydroxyphenyl)methanes, specifically tripodal diglycolamides and the use thereof for complexation and removal of lanthanides. Synthetic intermediates used are tris(3,5-dialkyl-2-hydroxyphenyl)methanes in which the OH group has been etherified with ω-amino- or cyanoalkyl groups. R. Mitra describes (Dalton Trans., 2007, 3924 to 3935) particular tris(2-hydroxyphenyl)methane derivatives which have terminal 2-pyridylmethylpiperazine groups. These molecules can bind zinc ions and are used as catalysts for phosphate diester synthesis. An intermediate disclosed in the multistage synthesis is tris[2-(2-hydroxylethoxy)-3-methyl-5-t-butylphenyl]methane.

EP-A 0 597 806 discloses glycidyl ethers containing cyclohexyl groups for use as reactive diluents, flexibilizers or adhesion improvers. Synthesis intermediates described include various tris(2-hydroxyphenyl)methanes, also including those in which the OH function has been etherified with a (substituted) 2-hydroxyethyl group. US 2009/0155714 discloses compositions for production of photoresists. Components used therefor include various tris(2-hydroxyphenyl)methane derivatives in which the OH function has been esterified with different carboxylic acids in each case.

It is known that surfactants aggregate above the critical micelle formation concentration (cmc) to form micelles. The shape of these water-soluble aggregates depends on the structure of the surfactants and on external parameters such as temperature or electrolyte concentration. Typically, spherical or rod-shaped micelles can form above the micelle formation concentration. Micelles can be characterized by means of NMR spectroscopy (see J. L. Lemyre in Langmuir 2010, 26 (9), 6250-6255). Given particular structural features and/or external parameters, it is also possible for long thread-like or worm-like micelles or associates to form.

A consequence of this is that, even at relatively low surfactant concentration, there is interlooping and overlapping of these long aggregates, which cause the viscosity of the surfactant solution to rise significantly. A particular minimum period of micelle stability is a prerequisite. This temporarily formed network of surfactant micelles, from a rheological point of view, reacts both in a viscose and elastic manner, which is why reference is generally made to viscoelastic surfactant solutions.

Micelles release individual surfactants, absorb surfactants into the micelle association, decompose and reform. Surfactant micelles which form viscoelastic networks are stable for very long periods before they fall apart into individual fragments and reform, such that the micellar network can offer resistance to shearing of the surfactant solution and hence reacts both in a viscose and elastic manner. Further details regarding surfactants which form viscoelastic, worm-like micelles, for example hexadecyltrimethylammonium p-toluenesulfonate or cetylpyridinium salicylate, are described, for example in H. Hoffmann et al. (Adv. Colloid Interface Sci. 1982, 17, 275 to 298) or M. R. Rojas (Journal of Colloid and Interface Science 342 (2010) 103 to 109).

On the basis of the properties described, viscoelastic surfactants are of very particular suitability as thickeners and can be used in various fields of industry.

US 2005/0155762 discloses betaines with alkyl chains of 14 to 24 carbon atoms, for example oleylamidopropylbetaine or erucylamidopropylbetaine, as thickening viscoelastic surfactants. These betaines, however, have industrial disadvantages, for example with regard to the stability thereof. U.S. Pat. No. 7,461,694 discloses zwitterionic surfactants with alkyl chains of 16 to 24 carbon atoms as viscoelastic surfactants.

WO 2008/100436 discloses a viscoelastic surfactant mixture composed of cationic, anionic or zwitterionic surfactants and a polymer. The surfactants have alkyl chain lengths of 12 to 25 carbon atoms.

In the disclosures cited, surfactants with long alkyl chains are used in each case for formation of viscoelastic surfactant solutions. One disadvantage of viscoelastic surfactants with long alkyl chains is that they solubilize nonpolar liquids on contact therewith, as a result of which the worm-like micelles are converted to spherical aggregates and the viscoelasticity is lost. Moreover, these viscoelastic surfactants, in contact with other surfactants, generally form mixed micelles, as a result of which the viscoelasticity is likewise lost.

Structures with short alkyl chains, or structures which deviate from the usual principle of linear construction of the surfactants, generally form spherical micelles or merely short anisometric aggregates, and hence do not form viscoelastic surfactant solutions.

Known viscoelastic surfactants are often cationic surfactants, such as hexadecyl-trimethylammonium p-toluenesulfonate or cetylpyridinium salicylate. Cationic surfactants with long alkyl radicals are of ecotoxicological concern (see, for example, Versteeg et al., Chemosphere 24 (1992) 641). Since they are adsorbed particularly efficiently on surfaces due to their positive charge, they additionally lose effectiveness in some applications. There is therefore a need for surfactants with a more favorable ecotoxicological profile and lower adsorption tendency.

It has now been found that, surprisingly, a suitable chemical modification of tris(2-hydroxyphenyl)methane gives rise to novel means of and processes for mineral oil production. The invention relates to a process for mineral oil production, in which an aqueous formulation comprising at least one derivative of tris(2-hydroxyphenyl)methane of the general formula (I) is injected into a mineral oil deposit through at least one injection well and the crude oil is withdrawn from the deposit through at least one production well,

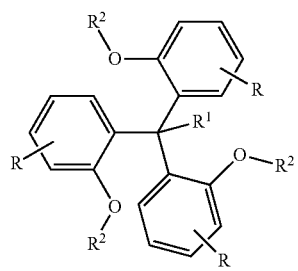
(I)

where the $R^1$, $R^2$ and R radicals in the formula (I) are each defined as follows:
R is in each case independently 0 to 4, preferably 1 to 2, $C_1$- to $C_{30}$-hydrocarbyl radicals per phenyl ring,
$R^1$ is a radical selected from the group of H, OH, F, Cl, Br, I and $C_1$- to $C_{30}$-hydrocarbyl groups, preferably H or OH,
$R^2$ are each independently radicals of the general formula (III), $$—(R^5—O—)_n—R^6—X \quad (III)$$

where n is a number from 1 to 50, preferably 8 to 35, and where the $R^5$ radicals are each independently selected from the group of $R^7$, $R^8$ and $R^9$ radicals, preferably from the group of $R^7$ and $R^8$,

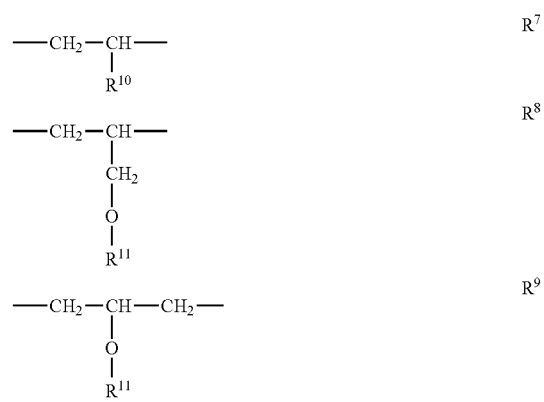

where $R^6$, X, $R^{10}$ and $R^{11}$ are each independently defined as follows:
$R^6$ is a single bond or an alkylene group having 1 to 10 carbon atoms, which may optionally have functional groups as substituents,
X is H or a hydrophilic group, especially an acidic end group,
$R^{10}$ is H or a $C_1$- to $C_6$-hydrocarbyl radical, preferably H or methyl,
$R^{11}$ is a $—(R^5—O—)_m—R^6—X$ group,
where m is a number from 0 to 50,
and where the total number z of all $R^5$ groups in one $R^2$ radical is 1 to 50, preferably 8 to 35, with the proviso that z is a number from 2 to 50 if at least one X is H.

These compounds are chemically and thermally stable, storable over a prolonged period, and useable even in salt-containing water at relatively high temperatures.

The invention also relates to a process for mineral oil production, in which the aqueous formulation used comprises, in which addition to water, at least one derivative of tris(2-hydroxyphenyl)methane of the general formula (II)

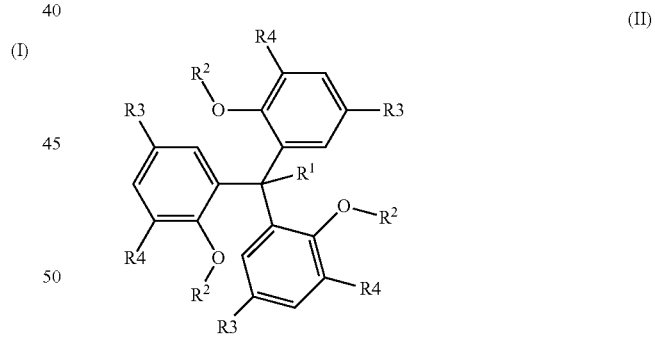
(II)

where $R^1$ and $R^2$ are each as defined above and $R^3$ and $R^4$ are each independently H or a $C_1$- to $C_{30}$-hydrocarbyl radical, especially a $C_1$- to $C_6$-hydrocarbyl radical, preferably a branched C4 radical, in particular t-butyl radicals.

The invention also relates to a process in which the compound of the formula (II) used is one in which all $R^3$ and $R^4$ are independently straight-chain or branched aliphatic $C_1$- to $C_6$-hydrocarbyl radicals, especially t-butyl radicals.

The invention also relates to a process in which X is an acid group selected from carboxyl groups —COOM, sulfo groups —$SO_3M$, sulfate groups —$OSO_3M$, phosphonic acid groups —$PO_2M_2$ or phosphoric acid groups —$OPO_3M_2$, where M is $H^+$ or a k-valent counterion $1/kY^{k+}$, especially Na, K or ammonium ions.

The invention also relates to a process in which X is an acidic group selected from carboxyl groups —COOM, sulfo groups —SO$_3$M or sulfate groups —OSO$_3$M, where M is H$^+$ or an alkali metal or alkaline earth metal counterion.

The invention also relates to a process wherein the R$^5$ radicals are R$^7$ and/or R$^8$ groups.

The invention also relates to a process in which the derivatives of tris(2-hydroxyphenyl)-methane used have a mean molar mass of 2000 to 3000 g/mol and the three 2-hydroxyphenyl groups are of the same structure.

The invention also relates to a process in which the temperature of the mineral oil deposit is 10 to 150° C., especially 10 to 120° C., often also 10 to 90° C.

The invention also relates to a process in which the aqueous formulation comprises, as a further component, at least one salt in an amount of 10 000 ppm to 350 000 ppm.

The invention also relates to a process in which the mineral oil production is effected from deposits with a very high salt content and a deposit temperature of 10 to 150° C., said deposit comprising, as well as mineral oil, also deposit water with a salinity of 10 000 ppm to 350 000 ppm, often 20 000 ppm to 350 000 ppm, especially of 100 000 ppm to 350 000 ppm, and the mineral oil having a viscosity (measured at deposit temperature) of at least 3 mPa*s, by injecting an aqueous formulation comprising at least one derivative of tris(2-hydroxyphenyl)methane of the formula (I) or of the formula (II) into the mineral oil deposit through at least one injection well and withdrawing crude oil from the deposit through at least one production well, said process comprising at least the following process steps:
    providing at least one tris(2-hydroxyphenyl)methane derivative of the general formula (I) or (II) as a pure substance, mixture or concentrate;
    preparing the aqueous formulation of the tris(2-hydroxyphenyl)methane component(s) by diluting the concentrate (K) provided in step (1) on site with water to a concentration of 0.01 g/l to 10 g/l, preferably of 0.05 g/l to 5 g/l,
    injecting the aqueous formulation of the tris(2-hydroxyphenyl)methane component(s) into the mineral oil formation, and
    withdrawing crude oil through at least one production well.

The invention also relates to a process wherein the derivative of tris(2-hydroxyphenyl)-methane used is an unbranched derivative and the concentration of the tris(2-hydroxyphenyl) methane derivative in the formulation is 0.01 g/l to 10 g/l, preferably 0.05 g/l to 5 g/l.

The invention also provides for the use of a tris(2-hydroxyphenyl)methane derivative of the formula (I) or of the formula (II) as described above as a thickener, especially as a viscoelastic thickener, in an aqueous formulation for mineral oil production.

The invention also relates to an aqueous formulation (for example in the form of a concentrate or ready-to-use composition), comprising, as components:
    0.001 to 99% by weight of at least one tris(2-hydroxyphenyl)methane derivative of the formula (I) according to claim 1,
    10 000 ppm to 350 000 ppm of inorganic salt, and optionally
    0.01 to 5% by weight of further auxiliary components for mineral oil production, and water and optionally further solvents.

The invention also relates to an aqueous formulation comprising:
    0.1 to 90% by weight of a tris(2-hydroxyphenyl)methane derivative of the formula (II)
    10 000 ppm to 350 000 ppm, often 50 000 ppm to 350 000 ppm of inorganic salt, and
    0.01 to 5% by weight of at least one auxiliary component from the group of surfactants, antioxidants and biocides, and water and optionally further solvents.

To flood the mineral oil deposit, an aqueous solution of the derivative (I) is injected into a mineral oil deposit through a well (called the injection well), and the mobility of the solution under formation conditions should correspond approximately to the mobility of the mineral oil. Suitable thickeners for the flooding must therefore also have the thickening effect under the conditions in the mineral oil deposit, i.e. also at temperatures above room temperature and in the presence of formation water with a high salt content. Formation waters may comprise up to 35% by weight of salts. The salts are, for example, alkali metal salts, or else alkaline earth metal salts. Formation temperatures may be up to 150° C.

It is a further object of the invention to provide a process for flooding mineral oil deposits, with which satisfactory results can also be achieved at relatively high formation temperatures and/or high salt contents.

Accordingly, a process has been found for mineral oil production, in which an aqueous formulation comprising at least one tris(2-hydroxyphenyl)methane derivative is injected into a mineral oil deposit through at least one injection well and crude oil is withdrawn from the deposit through at least one production well.

The amount of the tris(2-hydroxyphenyl)methane derivative in the formulation is preferably 0.01 to 10% by weight, often also 0.05 to 10% by weight (based on the overall formulation).

In a further preferred embodiment, the aqueous formulation further comprises salts in an amount of 10 000 ppm to 350 000 ppm.

It has been found that, surprisingly, the viscosity of the aqueous formulations used for the process changes only slightly with rising temperature. Even at relatively high temperatures (e.g. 75° C.) and in salt-rich solutions (for example greater than 30 000 ppm), precipitation of the tris(2-hydroxyphenyl)methane derivative (turbidity) can be avoided.

A particularly good ratio of viscosity achieved to amount of tris(2-hydroxyphenyl)methane derivative (I) used is achieved.

The invention can be specified as follows:

Tris(2-hydroxyphenyl)methane Derivatives Used

For the process according to the invention for mineral oil production, an aqueous formulation of at least one tris(2-hydroxyphenyl)methane derivative is used and is injected into a mineral oil deposit through an injection well.

The compounds used in accordance with the invention are derivatives of tris(2-hydroxyphenyl)methane of the general formula (I).

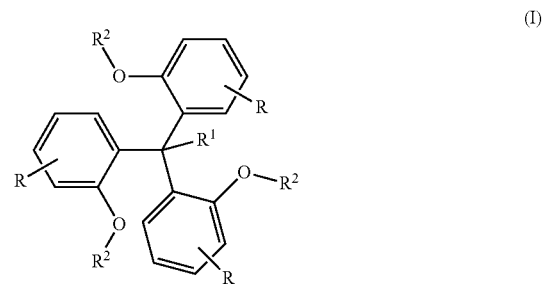

The R$^1$ radical is a radical selected from the group of H, OH, F, Cl, Br, I, and straight-chain, branched or cyclic, aliphatic and/or aromatic C$_1$- to C$_{30}$-hydrocarbyl groups. Preference is given to H, Cl, a straight-chain or branched C$_1$- to C$_{12}$-alkyl group or a benzyl group. R$^1$ is more preferably H.

The three phenyl rings may each independently be substituted in the 3, 4, 5 and 6 positions by hydrocarbyl radicals R having 1 to 30 carbon atoms, where the groups may be in any arrangement. Preference is given to 1 or 2 R groups per phenyl ring. The R groups may be straight-chain, branched or cyclic, aliphatic and/or aromatic hydrocarbyl radicals.

Preference is given preferably to straight-chain, branched or cyclic aliphatic hydrocarbyl groups having 1 to 20 and more preferably 1 to 12 carbon atoms. Examples of suitable R groups comprise methyl, ethyl, n-propyl, isopropyl, n-butyl, i-propyl, t-butyl, n-pentyl, 1,1-dimethylpropyl, 2,2-dimethylpropyl, 3-methylbutyl, hexyl, 2-ethylhexyl, heptyl, octyl, nonyl, decyl, undecyl, dodecyl, cyclopentyl, cyclohexyl, adamantyl or benzyl groups. The tert-butyl group is particularly suitable.

The compounds used in accordance with the invention preferably have the general formula (II).

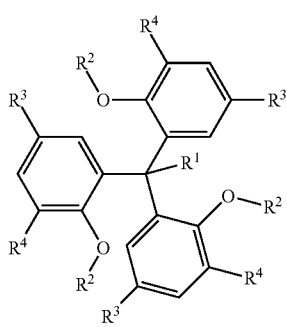

(II)

In formula (II), R$^3$ and R$^4$ are each independently H or hydrocarbyl radicals having 1 to 30 carbon atoms, preferably 1 to 20 carbon atoms and more preferably 1 to 12 carbon atoms. The hydrocarbyl radicals may be straight-chain, branched, cyclic, aliphatic and/or aromatic. They are preferably straight-chain, branched or cyclic aliphatic hydrocarbyl groups having 1 to 20 and more preferably 1 to 12 carbon atoms, and most preferably straight-chain or branched aliphatic hydrocarbyl groups having 1 to 6 carbon atoms.

Examples of suitable hydrocarbyl groups comprise methyl, ethyl, propyl, isopropyl, n-butyl, i-butyl, t-butyl, n-pentyl, 1,1-dimethylpropyl, 2,2-dimethylpropyl, 3-methylbutyl, hexyl, 2-ethylhexyl, heptyl, octyl, nonyl, decyl, undecyl, dodecyl, cyclopentyl, cyclohexyl or adamantyl groups. The R$^3$ and R$^4$ radicals are preferably H or methyl, ethyl, propyl, isopropyl, n-butyl, i-butyl, t-butyl, n-pentyl, 1,1-dimethylpropyl, 2,2-dimethylpropyl, 3-methylbutyl groups, 1,1,3,3-tetramethylbutyl, more preferably t-butyl groups.

In a preferred embodiment of the invention, at least one of the R$^3$ and R$^4$ radicals is not H; more preferably, the R$^3$ radical in this embodiment is not H. Most preferably, both R$^3$ and R$^4$ radicals are not H. Preferred, particularly preferred and very particularly preferred combinations of R$^3$ and R$^4$ radicals are specified in Tables 1, 2 and 3 below:

TABLE 1

List of preferred combinations of substituents

| R$^3$ | R$^4$ |
|---|---|
| t-Butyl | H |
| t-Butyl | Methyl |
| t-Butyl | Ethyl |
| t-Butyl | t-Butyl |
| Me | Me |
| Me | tBu |
| 1,1-Dimethylpropyl | H |
| 1,1-Dimethylpropyl | Methyl |
| 1,1-Dimethylpropyl | Ethyl |
| 1,1-Dimethylpropyl | t-Butyl |
| 1,1-Dimethylpropyl | 1,1-Dimethylpropyl |
| 1,1,3,3-Tetramethylbutyl | 1,1,3,3-Tetramethylbutyl |
| t-Butyl | 1,1,3,3-Tetramethylbutyl |

TABLE 2

List of preferred combinations of substituents

| R$^3$ | R$^4$ |
|---|---|
| t-Butyl | Methyl |
| t-Butyl | t-Butyl |
| 1,1-Dimethylpropyl | Methyl |
| 1,1-Dimethylpropyl | 1,1-Dimethylpropyl |
| 1,1,3,3-Tetramethylbutyl | 1,1,3,3-Tetramethylbutyl |
| t-Butyl | 1,1,3,3-Tetramethylbutyl |

TABLE 3

List of preferred combinations of substituents

| R$^3$ | R$^4$ |
|---|---|
| t-Butyl | t-Butyl |
| 1,1-Dimethylpropyl | 1,1-Dimethylpropyl |
| 1,1,3,3-Tetramethylbutyl | 1,1,3,3-Tetramethylbutyl |
| t-Butyl | 1,1,3,3-Tetramethylbutyl |

Most preferably, both R$^3$ and R$^4$ are tert-butyl radicals.

The R$^2$ radicals in the abovementioned formulae (I) and (II) are each independently radicals of the general formula

(III).

The R$^5$ radicals in formula (III) are each independently groups selected from the group of R$^7$, R$^8$ and R$^9$ radicals

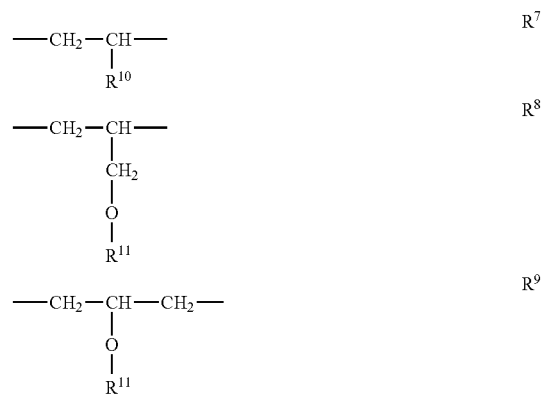

The R$^{10}$ radicals in the R$^7$ groups here are each independently H or a hydrocarbyl radical having 1 to 6 carbon atoms, preferably an aliphatic hydrocarbyl radical having 1 to 6 carbon atoms. Instead of the —$CH_2$—$CH(R^{10})$— arrangement shown in formula (III), the alkylene group may also be incorporated into the polyoxyalkylene chain in inverse arrangement —$CH(R^{10})$—$CH_2$—. The formula (III) is supposed to encompass both arrangements, and it is of course also possible for both arrangements to be present in one chain. Examples of $R^{10}$ radicals comprise H and methyl, ethyl, n-propyl or phenyl radicals. More particularly, $R^{10}$ is H, methyl, ethyl or n-propyl radicals, preferably H, methyl or ethyl radicals, more preferably H or methyl.

In the $R^8$ and $R^9$ groups, the $R^{11}$ groups are groups of the general formula —$(R^5$—O—$)_m$—$R^6$—X where m is a number from 0 to 50. The group may thus (in the case that m=0) be a —$R^6$—X group joined directly to the oxygen atom, or (in the case that m>0) a group in which —$R^6$—X is joined to the oxygen atom via a polyalkoxy group. Due to the fact that $R^{11}$ in the latter case may itself in turn comprise $R^8$ and $R^9$ groups, the $R^2$ groups may also be multiply branched.

The $R^7$, $R^8$ and $R^9$ radicals may be arranged as desired in the $R^2$ radicals, for example randomly, in blocks, in an alternating manner or with a gradient.

Compounds of the formula (I) or (II) used with preference are structures with pure ethylene oxide chains with mean chain lengths between 6-15 EO units. Particular preference is also given to EO-glycidol copolymers with 6-12 EO units and 1-5 glycidol units. Among these, copolymers with a block copolymer structure are particularly suitable.

In the above radicals, X is in each case H or a hydrophilic group. Preferably, a hydrophilic group comprises one or more oxygen atoms. According to the type of $R^2$ radical, it is possible for only one X group or else a plurality of X groups to be present in one $R^2$ radical. Hydrophilic groups may especially be acidic groups, preferably a group selected from the group of carboxyl groups —COOM, sulfo groups —$SO_3M$, sulfate groups —$OSO_3M$, phosphonic acid groups —$PO_2M_2$ or phosphoric acid groups —$OPO_3M_2$, where M is $H^+$ or a k-valent counterion $1/kY^{k+}$. The acidic groups may thus be present as the free acid and/or as a salt thereof. When M is not $H^+$, it is preferably a monovalent counterion, for example $NH_4^+$, ammonium ions with organic radicals or alkali metal ions. Preferred acidic groups are those selected from the group of carboxyl groups —COOM, sulfo groups —$SO_3M$ and sulfate groups —$OSO_3M$, more preferably sulfate groups —$OSO_3M$.

Preferred hydrophilic groups further comprise radicals which comprise at least one, preferably at least 2, OH groups, especially mono- or oligosaccharide radicals, preferably monosaccharide radicals. The saccharides may in principle be all kinds of saccharides. It is possible with preference to use radicals derived from pentoses and hexoses, especially from hexoses. Examples of suitable monosaccharides comprise glucose, mannose, galactose, fructose or ribose. It is possible with preference to use radicals derived from glucose. Derivatives of the saccharides may also be involved, for example products originating from the saccharides through reduction or oxidation. More particularly, such derivatives may be sugar acids, for example gluconic acid.

Examples of other hydrophilic groups comprise, for example, amine oxide groups.

$R^6$ is a single bond or an alkylene group having 1 to 10 carbon atoms, preferably 1 to 3 carbon atoms, which may optionally have functional groups as substituents, especially an OH group. Examples of suitable groups comprise —$CH_2$—, —$CH_2CH_2$—, —$CH_2$—$CH_2$—$CH_2$— or —$CH_2$—CH(OH)—$CH_2$— groups.

The total number of all $R^5$ groups in one $R^2$ radical, i.e. of the $R^5$ groups in the main group, and also of the $R^5$ groups in any branches present, shall be referred to hereinafter by z. In the case that $R^2$ is a linear group, z corresponds to the number n.

According to the invention, z is a number from 2 to 50 in the case that at least one X is H, and is a number from 1 to 50 in the case that no X is H. The numbers z, n and m relate in a known manner to the mean number of alkoxy groups present in the molecule, where the mean need not of course be a natural number, but may also be a positive rational number.

In general, z, irrespective of the nature of substituent X, is a number from 2 to 50, especially 4 to 40, preferably 5 to 30, more preferably 8 to 20 and most preferably 10 to 15.

The person skilled in the art makes an appropriate selection among the possible groups (III) and of the $R^1$, $R^2$, $R^3$ and $R^4$ radicals according to the desired end use of the compounds in mineral oil production.

In a first preferred embodiment of the invention, at least one of the $R^5$ radicals is an $R^7$ radical. In a particularly preferred embodiment of the invention, all $R^5$ radicals are $R^7$ radicals. When the $R^7$ radicals comprise different $R^{10}$ radicals, they may be arranged in any manner, for example randomly, in blocks, in an alternating manner or with a gradient. At least some of the z $R^{10}$ radicals are preferably H, especially at least 20%, preferably at least 50%, more preferably at least 80%, and most preferably all $R^{10}$ radicals are H.

In a preferred embodiment of the invention, the $R^2$ radicals are —$(R^7$—O—$)_n$—$R^6$—X groups (IIIa). $R^8$ radicals and $R^9$ radicals are not present in this embodiment.

Particular preference is given to —$(R^7$—O—$)_n$—H groups (IIIb), i.e. X=H and $R^6$ is a single bond.

In (IIIa) and (IIIb), n is a number from 5 to 30, more preferably 8 to 20 and most preferably 10 to 15. The $R^{10}$ radicals in the $R^7$ radicals, i.e. the —$CH_2$—$CH(R^{10})$— radicals, are each independently a radical selected from the group of H, methyl and ethyl, where at least 50% of the radicals ($R^{10}$) are H, preferably at least 80% of the radicals and most preferably all $R^{10}$ radicals are H. When a plurality of different $R^{10}$ radicals are present, they may be arranged randomly, in an alternating manner or in blocks. In the case of blockwise arrangement, it is preferable when the ethylene oxide groups (i.e. $R^{10}$=H) form the terminal block.

In a further preferred embodiment of the invention, the $R^2$ radicals are —(—$CH_2$—$CH(R^{12})$—O—$)_a$—(—$CH_2$—$CH_2$—O—$)_b$—H groups (IIIc), where the two blocks are arranged in this sequence. This is thus again an embodiment in which only $R^7$ groups are present, X is H and $R^6$ is a single bond. The $R^{12}$ radicals in the formula (IIIc) are hydrocarbyl radicals having 1 to 6 carbon atoms, preferably aliphatic hydrocarbyl radicals having 1 to 6 carbon atoms, preferably a methyl and/or ethyl group. a is numbers from 1 to 49, preferably 1 to 10, and b is numbers from 1 to 49, preferably 1 to 20, with the proviso that a+b=n=2 to 50. Preferably, b≥a.

In a further preferred embodiment of the invention, the $R^2$ radicals are —(—$CH_2$—$CH(R^{13})$—O—$)_n$—$R^6$—X groups (IIId), where the X radical in at least one of the $R^2$ groups is not H. The $R^{10}$ radicals in the formula (IIId) are each independently a radical selected from the group of H, methyl and ethyl, where at least 20% of the $R^{10}$ radicals are H, preferably at least 50% of the radicals, more preferably at least 80% of the radicals, and most preferably all $R^{10}$ radicals are H. When a plurality of different $R^{13}$ radicals are present, they may be arranged randomly, in an alternating manner or in blocks. In the case of blockwise arrangement, it is preferable when the ethylene oxide groups (i.e. $R^{13}$=H) form the terminal block.

Preferably, X in formula (IIIc) comprises carboxyl groups —COOM, sulfo groups —SO$_3$M, sulfate groups —OSO$_3$M. For example, the groups may be —(—CH$_2$—CH(R$^{13}$)—O—)$_n$—H groups in combination with —(—CH$_2$—CH(R$^{13}$)—O—)$_n$—SO$_3$H groups. In this embodiment, n is preferably numbers from 1 to 30.

In a further preferred embodiment of the invention, the R$^2$ radicals of the general formula —(R$^6$—O—)$_n$—R$^6$—X (III) are R$^8$ and/or R$^9$ radicals. They may thus either be radicals which comprise exclusively R$^8$ and/or R$^9$ groups or those which, as well as R$^8$ and/or R$^9$, additionally comprise R$^7$ groups. R$^7$ are preferably R$^7$ groups where R$^{10}$=H, i.e. groups derived from ethylene oxide.

In a further preferred embodiment of the invention, R$^2$ comprises radicals of the general formula —(—CH$_2$CH(CH$_2$OH)—O—)$_c$(CH$_2$CH(R$^{14}$)—O—)$_d$—R$^6$—X (IIIe), where the sum of c+d=z. Formula (IIIe) involves monomers R$^7$ and R$^8$ where R$^{11}$ is H. The R$^{14}$ radicals in the formula (IIIe) are each independently a radical selected from the group of H, methyl and ethyl, where at least 20% of the R$^{10}$ radicals are H, preferably at least 50% of the radicals, more preferably at least 80% of the radicals, and more preferably all R$^{14}$ radicals are H. In this embodiment, R$^6$ is preferably a single bond and X is preferably H.

A further embodiment of the invention involves derivatives of tris(2-hydroxyphenyl)methanes which are obtainable by free-radically polymerizing vinyl carboxylates in the presence of compounds of the general formulae (I) and (II).

The polymerization of vinyl carboxylates in the presence of polyalkoxy groups is known in principle to those skilled in the art. In this reaction, vinyl ester, oligovinyl ester and/or polyvinyl ester groups graft onto the polyalkoxy groups, i.e. the result is polyalkoxy groups having additional side groups. The polyvinyl ester groups are subsequently hydrolyzed at least partially to OH groups. The OH groups can subsequently optionally be functionalized with —R$^6$—X groups. The reaction scheme is illustrated below by way of example.

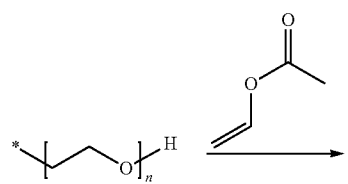

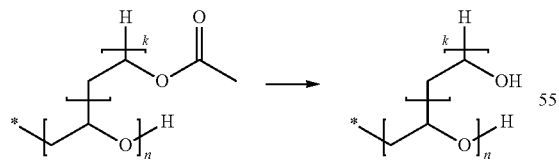

Suitable vinyl carboxylates comprise especially vinyl formate, vinyl acetate and vinyl propionate. Particularly suitable for modification are especially compounds which have (IIIb) or (IIIc) groups.

To prepare the inventive compounds, it is first possible to synthesize tris(2-hydroxyphenyl)methane compounds of the general formulae (IV) and (V) with the desired substitution pattern in terms of R$^1$, and R or R$^3$ and R$^4$.

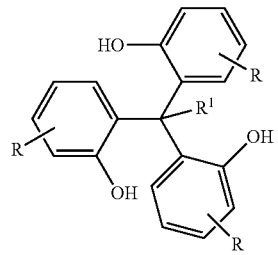

(IV)

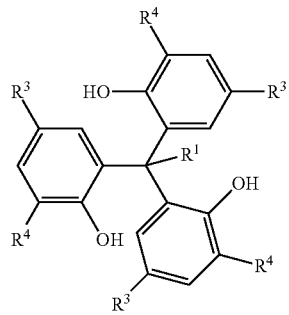

(V)

The methods for preparation of the compounds are described in detail in the literature cited at the outset, for example G. Casiraghi (Tetrahedron Letters, No. 9, 679 to 682 (1973)), M. B. Dinger (Chem. Commun., 1999, 2525/2526, Inorg. Chem. 2000, 39, 1238 to 1254) and (Inorg. Chem. 2001, 40, 1029 to 1036), M. B. Dinger (Eur J. Org. Chem. 2000, 2467 to 2478), K. Matloka (Dalton Trans., 2005, 3719 to 3721), M. W. Peters (Inorg. Chem., 2002, 41, 1701 to 1716) and by R. Mitra (Dalton Trans., 2007, 3924 to 3935).

The tris(2-hydroxyphenyl)methane compounds of the general formulae (IV) and (V) can be alkoxylated in a manner known in principle in a second step. The performance of alkoxylations is known in principle to those skilled in the art. It is likewise known to those skilled in the art that the reaction conditions, especially the selection of the catalyst, can influence the molecular weight distribution of the alkoxylates. For the alkoxylation, C$_2$- to C$_8$-alkylene oxides are used, for example ethylene oxide, propylene oxide, butylene oxide or styrene oxide. Preference is given in each case to the 1,2-alkylene oxides. The use of these alkylene oxides leads to groups which comprise R$^7$ radicals.

In order to obtain R$^8$ and R$^9$ radicals, glycidol (VIa) or glycidol (VIb) protected with a suitable protecting group R$^{15}$ (VIa)

△—CH$_2$OH (VIb)

△—CH$_2$O—R$^{15}$ is used as the alkene oxide. R$^{15}$ may in principle be all kinds of groups with which the OH function can be protected during the alkoxylation. They can be eliminated in a manner known in principle after the alkoxylation, or else only after introduction of the —R$^6$—X groups. R$^{15}$ may, for example, be a t-butyl group or a benzyl group.

Since, after the reaction of the unprotected glycidol, two OH groups present in the chain can react further, there is formation of the branches already cited in the R² radical. With the aid of the protected glycidol, it is possible in a controlled manner to introduce R⁸ groups of the formula —CH₂—CH(CH₂OH)— into the R² radical.

The alkoxylation may be a base-catalyzed alkoxylation. For this purpose, the tris(2-hydroxyphenyl)methane compounds can be admixed in a pressure reactor with alkali metal hydroxides, preferably potassium hydroxide, or with alkali metal alkoxides, for example sodium methoxide. By means of reduced pressure (for example <100 mbar) and/or an increase in the temperature (30 to 150° C.), water still present in the mixture can be drawn off. Thereafter, the alcohol is present as the corresponding alkoxide. Subsequently, inert gas (e.g. nitrogen) is used for inertization and the alkylene oxide(s) is/are added stepwise at temperatures of 60 to 180° C. up to a pressure of max. 10 bar. At the end of the reaction, the catalyst can be neutralized by addition of acid (e.g. acetic acid or phosphoric acid) and can be filtered off if required.

The catalyst can also be removed by addition of commercial standard silicates, which are subsequently filtered off. Optionally, the alkoxylation can also be performed in the presence of a solvent. This may be, for example, toluene, xylene, dimethylformamide or ethylene carbonate. The alkoxylation can also be accelerated by addition of crown ethers, for example by the addition of [18]-crown-6.

The alkoxylation of the alcohols can, however, also be undertaken by means of other methods, for example by acid-catalyzed alkoxylation. The acids may be protic acids or Lewis acids (for example BF₃). It is also possible to use, for example, double hydroxide clays as described in DE 43 25 237 A1, or it is possible to use double metal cyanide catalysts (DMC catalysts).

Suitable DMC catalysts are disclosed, for example, in DE-A 102 43 361, especially paragraphs [0029] to [0041], and the literature cited therein. For example, it is possible to use catalysts of the Zn—Co type. To perform the reaction, the alcohol R—OH can be admixed with the catalyst, and the mixture can be dewatered as described above and reacted with the alkylene oxides as described. Typically not more than 1000 ppm of catalyst based on the mixture are used, and the catalyst can remain in the product due to this small amount.

The amount of catalyst may generally be less than 1000 ppm, for example 250 ppm or less.

The alkoxylation can alternatively also be undertaken by reaction of the compounds (IV) and (V) with cyclic carbonates, for example ethylene carbonate.

By means of the alkoxylation, inventive compounds are obtained directly, mainly those where X=H. These have terminal OH groups. This is shown in figures (VII) and (VIII) below, by way of example with inventive compounds which have polyalkoxy chains composed of R⁷ groups.

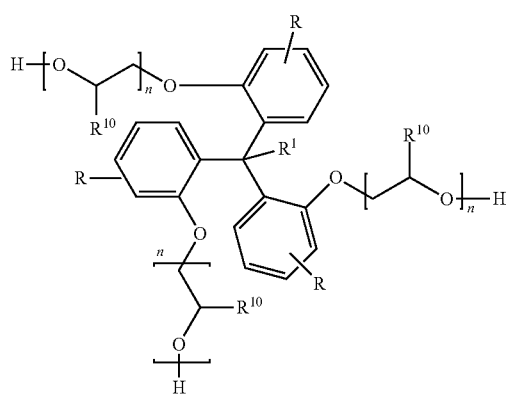

(VII)

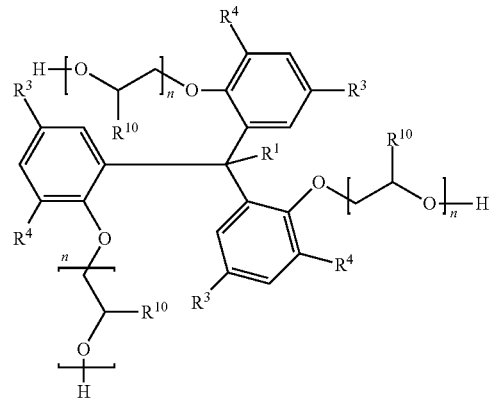

(VIII)

To introduce X groups which are not H, the alkoxylated tris(2-hydroxyphenyl)methane derivatives of the formula (VII) or (VIII) having terminal OH groups are functionalized further with —R⁶—X groups in a suitable manner. This gives compounds of the general formula (IX) or (X).

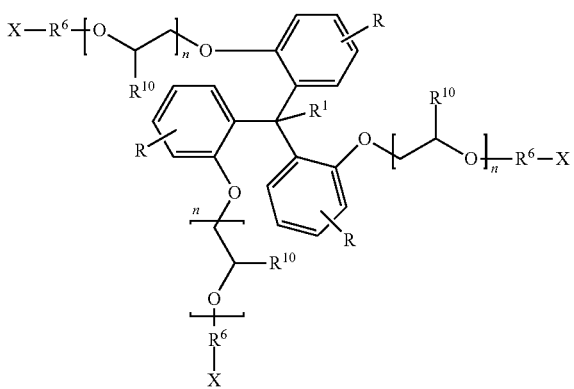

(IX)

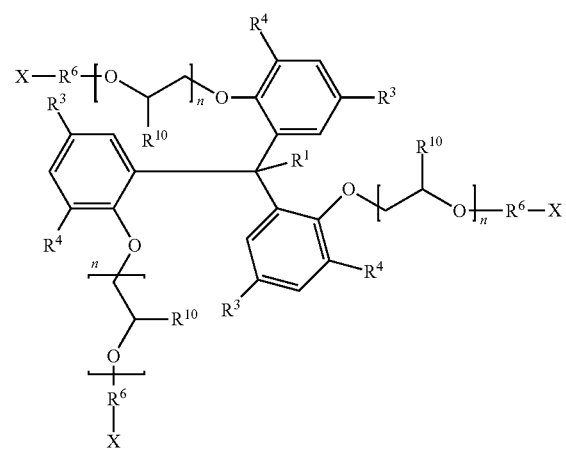

(X)

Derivatives comprising sulfate groups —OSO₃M can be obtained by reaction of the terminal OH groups with SO₃, sulfuric acid, chlorosulfuric acid or aminosulfonic acid (CAS No. 5329-14-6) and subsequent neutralization with, for example, sodium hydroxide solution. This can be performed, for example, in a falling-film reactor. This reaction substitutes only the terminal OH groups with sulfate groups. $R^6$ in this reaction is a double bond.

Derivatives comprising sulfonate groups —$SO_3M$ can be obtained by substitution of the OH group for Cl using phosgene or thionyl chloride. The conversion can be undertaken in the presence of a solvent, for example chlorobenzene. HCl released and $CO_2$ or $SO_2$ released can advantageously be removed from the system by stripping with nitrogen, such that ether cleavage is suppressed. The alkyl alkoxy chlorine compound is subsequently reacted with an aqueous solution of sodium sulfite, the chloride being substituted by sulfite to obtain the sulfonate. The substitution can be undertaken in the presence of a phase mediator (for example $C_1$- to $C_8$-alcohols) at a temperature of 100 to 180° C. under pressure.

The sulfonates can alternatively be obtained by addition of vinylsulfonic acid onto the compound (V) (or else onto VII or VIII). Details thereof are described, for example, in EP-A 311 961. Sulfonates can also be obtained by reacting the compounds (V) (or else VII or VIII) with 1,3-propane sultone or 1,4-butane sultone. This gives sulfonates with a terminal —$CH_2$—$CH_2$—$CH_2$—$SO_3M$ (i.e. $R^6$=$CH_2$—$CH_2$—$CH_2$—) or —$CH_2$ —$CH_2$—$CH_2$—$CH_2$—$SO_3M$ (i.e. $R^6$=$CH_2$—$CH_2$—$CH_2$—$CH_2$—) group. Compounds with a terminal —$CH_2$—$CH(OH)$—$CH_2$—$SO_3M$ group (i.e. $R^6$=—$CH_2$—$CH(OH)$—$CH_2$—) can be obtained by reaction of the compound (V) with epichlorohydrin and subsequent nucleophilic substitution of the chloride group by sodium sulfite.

Derivatives comprising carboxylate groups —COOM can be obtained by oxidation of the compound (V) (or else VII or VIII). All oxidizing agents are suitable for this purpose, optionally in combination with suitable catalysts which can oxidize the terminal OH group of the compound (V) to the COOH group, without oxidizing other parts of the molecule to any great extent. The oxidation can be undertaken, for example, with the aid of air or oxygen using a noble metal catalyst (for example a catalyst based on palladium). This synthesis variant gives a terminal —$CH_2$—COOM group (i.e. $R^6$=—$CH_2$—). Carboxylates can additionally also be prepared by adding (meth)acrylic acid or a (meth)acrylic ester onto the OH groups by means of a Michael addition. If the esters are used, these are hydrolyzed after the addition. This synthesis variant—according to whether acrylic acid or (meth)acrylic acid or esters thereof have been used—gives terminal —$CH_2$—$CH_2$—COOM or —$CH_2$—$CH(CH_3)$—COOM groups. Carboxylate groups COOM can also be obtained by reaction of the compounds (VII) or (VIII) with chloroacetic acid $ClCH_2COOH$ or salts thereof $ClCH_2COOM$ in the presence of a base.

Phosphate groups can be introduced by reaction with phosphorus pentoxide, phosphonate groups by reaction with vinylphosphonic acid.

Compounds with mono- or oligosaccharide groups can be prepared by converting the appropriate saccharide, for example glucose, with the aid of an acidic catalyst, for example para-toluenesulfonic acid, and n-butanol to the corresponding butyl acetal. The water of reaction which forms can be removed from the reaction mixture by application of reduced pressure. Thereafter, the compound (V) (or else VII or VIII) is added and the transacetalization is driven by distillative removal of the butanol from the equilibrium. The acidic catalyst can be neutralized at the end of the reaction by addition of base, for example NaOH or KOH.

According to the type of $R^2$ groups, the compounds obtained have only one terminal —$R^6$—X group, or else several terminal and/or pendant —$R^6$—X groups.

In the case of introduction of the terminal —$R^6$—X group, it is of course not necessary to convert all OH groups of the H-terminated inventive compounds. It is possible to convert only a portion of the groups, for example only every third group on average. In this way, it is possible to adapt the properties of the inventive compounds to the desired end use.

In the case of glycidol, various synthesis variants are conceivable. If unprotected glycidol is used, the $R^2$ groups may be branched and have several terminal or lateral OH groups. These groups may be converted fully or else only partly to —$R^6$—X groups. In the case of only partial conversion, the conversion is random.

If protected glycidol (VIb) is used, what is formed first of all is an unbranched polyalkoxy chain with a terminal OH group and pendant protected OH groups. The protecting groups can then first be removed and then the introduction of the —$R^6$—X groups can be undertaken.

In this case, what is formed is a linear $R^2$ group which has terminal and/or pendant —$R^6$—X groups. If, in an alternative synthesis, the protecting groups are not eliminated at first, but the introduction of the —$R^6$—X groups is undertaken first, only the terminal OH groups react. The detachment of the protecting groups may follow. In this case, what is formed is an $R^2$ group which has a terminal —$R^6$—X group and additionally pendant methylol groups —$CH_2OH$.

To execute the process according to the invention, at least one production well and at least one injection well are sunk into the mineral oil deposit. In general, a deposit is provided with several injection wells and with several production wells.

Through the at least one injection well, an aqueous formulation of the tris(2-hydroxyphenyl)methane derivative (I) described is injected into the mineral oil deposit, and mineral oil is withdrawn from the deposit through at least one production well. The term "mineral oil" in this context does not mean only single-phase oil; instead, the term also comprises the customary crude oil-water emulsions. By virtue of the pressure generated by the formulation injected, the mineral oil flows in the direction of the production well and is produced via the production well.

The deposit temperature of the mineral oil deposit to which the process according to the invention is applied is, in accordance with the invention, 10 to 150° C., preferably 10° C. to 120° C. and, for example, 20° C. to 70° C.

The person skilled in the art is aware that a mineral oil deposit often has a homogeneous temperature based on time and area, except in the case of thermal measures. The deposit temperature mentioned is based on the region of the deposit between the injection and production wells, which is covered by the injected composition. Methods for determination of the temperature of a mineral oil deposit are known in principle to those skilled in the art.

The temperature is generally undertaken from temperature measurements at particular sites in the formation.

The process according to the invention can be employed especially in the case of mineral oil deposits with an average permeability of 100 mD to 154 D, preferably 150 mD to 2 D and more preferably 200 mD to 1 D. The permeability of a mineral oil formation is reported by the person skilled in the art in the unit of "darcies" (abbreviated to "D" or "MD" for "millidarcies"), and can be determined from the flow rate of a liquid phase in the mineral oil formation as a function of the pressure differential applied. The flow rate can be determined in core flooding tests with drill cores taken from the formation.

Details thereof can be found, for example, in K. Weggen, G. Pusch, H. Rischmüller in "Oil and Gas", pages 37 ff., Ullmann's Encyclopedia of Industrial Chemistry, Online edition, Wiley-VCH, Weinheim 2010. It is clear to the person skilled in the art that the permeability in a mineral oil deposit need not be homogeneous, but generally has a certain distribution, and the specification of the permeability of a mineral oil deposit is accordingly an average permeability.

To execute the process, an aqueous formulation comprising, as well as water, at least the tris(2-hydroxyphenyl)methane derivative (I) described is used. It is also possible to use mixtures of different tris(2-hydroxyphenyl)methane derivatives. The formulation can be made up in freshwater, or else in water containing salts. Mixtures of different salts may be involved.

For example, it is possible to use seawater to make up the aqueous formulation, or it is possible to use produced formation water which is reused in this manner. In the case of offshore production platforms, the formulation is generally made up in seawater. In the case of onshore production facilities, the tris(2-hydroxyphenyl)methane derivative can advantageously first be dissolved in freshwater, and the resulting solution can be diluted to the desired use concentration with formation water. The formulation can preferably be produced by initially charging the water, scattering in the tris(2-hydroxyphenyl)methane derivative as a powder and mixing it with the water.

The salts may especially be alkali metal salts and alkaline earth metal salts. Examples of typical cations comprise $Na^+$, $K^+$, $Mg^{2+}$ or $Ca^{2+}$ and $Mg^{2+}$. Examples of typical anions comprise chloride, bromide, hydrogencarbonate, sulfate or borate.

When the formulation comprises salts, generally at least one or more than one alkali metal ion is present, especially at least $Na^+$. In addition, it is also possible for alkaline earth metal ions to be present, in which case the weight ratio of alkali metal ions/alkaline earth metal ions is generally $\geq 2$, preferably $\geq 3$. The anions present are generally at least one or more than one halide ion, especially at least $Cl^-$. In general, the amount of $Cl^-$ is at least 50% by weight, preferably at least 80% by weight, based on the sum of all anions.

The total amount of all salts in the aqueous formulation is frequently 10 000 ppm to 350 000 ppm (parts by weight), based on the sum of all components of the formulation.

When seawater is used to make up the formulation, the salt content is generally 20 000 ppm to 50 000 ppm and, when formation water is used, generally 100 000 ppm to 250 000 ppm. The amount of alkaline earth metal ions may preferably be 1000 to 53 000 ppm. The aqueous formulation may also comprise further components, for example biocides, stabilizers and inhibitors.

The concentration of the tris(2-hydroxyphenyl)methane derivative is fixed such that the aqueous formulation has the desired viscosity for the end use. The viscosity of the formulation should generally be at least 3 mPas (measured at 25° C. and a shear rate of, for example, 7 $s^{-1}$, or as preferentially occurs in the reservoir), preferably at least 10 mPas.

According to the invention, the concentration of the tris(2-hydroxyphenyl)methane derivative in the formulation is 0.01 to 10% by weight, often 0.05 to 10% by weight, based on the sum of all components of the aqueous formulation. Preferably, the amount is 0.05 to 5% by weight, more preferably 0.05 to 1% by weight and, for example, approx. 0.1% by weight.

The injection of the aqueous formulation can be undertaken by means of customary apparatus.

The formulation can be injected into one or more injection wells by means of customary pumps. The injection wells are often lined with steel tubes cemented in place in the region of the mineral oil deposit, and the steel tubes are perforated at the desired point. The formulation enters the mineral oil formation from the injection well through the perforation. In a manner known in principle, the pressure applied by means of the pumps fixes the flow rate of the formulation and hence also the shear stress with which the aqueous formulation enters the formation. The shear stress on entry into the formation can be calculated by the person skilled in the art in a manner known in principle on the basis of the Hagen-Poiseuille law using the flow area on entry into the formation, the mean pore radius and the volume flow rate. The average permeability or porosity of the formation can be determined in a manner known in principle by measurements on drill cores. Of course, the greater the volume flow rate of aqueous formulation injected into the formation, the greater the shear stress.

The rate of injection can be fixed by the person skilled in the art according to the properties of the formation (permeability, thickness) and the requirements of the mineral oil field (number of injectors, configuration thereof, etc.).

Preferably, the shear rate on entry of the aqueous formulation into the formation is at least 30 000 $s^{-1}$, preferably at least 60 000 $s^{-1}$ and more preferably at least 90 000 $s^{-1}$.

Tris(2-hydroxyphenyl)methane derivatives of the formula (I) particularly preferred for execution of the process are the components which follow.

These products can be stored and transported as solids, and are storage-stable per se, but can also be provided as aqueous solutions or compositions with further components.

In the products specified below, the base element tris(3,5-di-tert-butyl-2-hydroxy-phenyl)methane is abbreviated to TRIS:

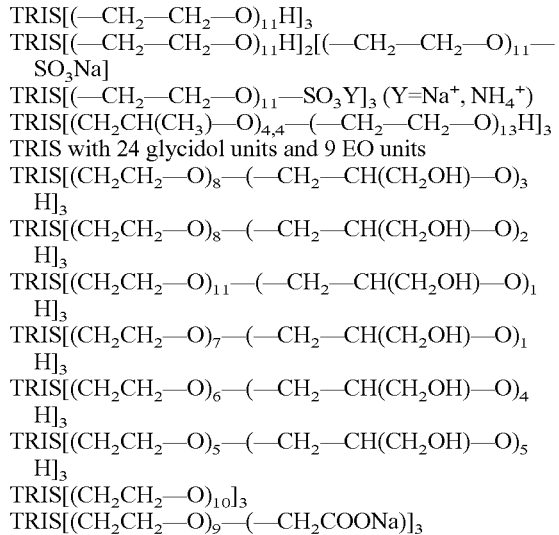

TRIS[(—$CH_2$—$CH_2$—O)$_{11}$H]$_3$
TRIS[(—$CH_2$—$CH_2$—O)$_{11}$H]$_2$[(—$CH_2$—$CH_2$—O)$_{11}$—$SO_3Na$]
TRIS[(—$CH_2$—$CH_2$—O)$_{11}$—$SO_3Y$]$_3$ (Y=$Na^+$, $NH_4^+$)
TRIS[($CH_2CH(CH_3)$—O)$_{4,4}$—(—$CH_2$—$CH_2$—O)$_{13}$H]$_3$
TRIS with 24 glycidol units and 9 EO units
TRIS[($CH_2CH_2$—O)$_8$—(—$CH_2$—$CH(CH_2OH)$—O)$_3$H]$_3$
TRIS[($CH_2CH_2$—O)$_8$—(—$CH_2$—$CH(CH_2OH)$—O)$_2$H]$_3$
TRIS[($CH_2CH_2$—O)$_{11}$—(—$CH_2$—$CH(CH_2OH)$—O)$_1$H]$_3$
TRIS[($CH_2CH_2$—O)$_7$—(—$CH_2$—$CH(CH_2OH)$—O)$_1$H]$_3$
TRIS[($CH_2CH_2$—O)$_6$—(—$CH_2$—$CH(CH_2OH)$—O)$_4$H]$_3$
TRIS[($CH_2CH_2$—O)$_5$—(—$CH_2$—$CH(CH_2OH)$—O)$_5$H]$_3$
TRIS[($CH_2CH_2$—O)$_{10}$]$_3$
TRIS[($CH_2CH_2$—O)$_9$—(—$CH_2COONa$)]$_3$ The invention also relates to an aqueous formulation comprising 0.1 to 90% by weight of a tris(2-hydroxyphenyl)methane derivative from the abovementioned group, and comprising 50 000 ppm to 350 000 ppm of inorganic salt, and (optionally) 0.01 to 5% by weight of at least one auxiliary component from the group of surfactants, antioxidants and biocides, and water and optionally further solvents.

The derivatives (I) of tris(2-hydroxyphenyl)methane described can be used to produce various formulations for mineral oil production, as described above. Also particularly suitable are the TRIS derivatives which comprise both EO units and glycidol units.

Frequently used concentrations and further components:
A) concentrations are often in the range of 0.01-10% by weight, often 0.05-10% by weight, preferred concentrations are between 0.1-1% by weight and particularly preferred concentrations between 0.1 and 0.5% by weight, based in each case on the overall formulation.

B) solvents can be used as further component. Typically, the derivative of tris(2-hydroxyphenyl)methane is dissolved in the formation water. Dissolution in seawater is also possible. Predissolution with a water-miscible solvent, e.g. ethanol or isopropanol, to prepare concentrates with higher active content is possible. It is also possible to use spring water.

C) salts influence the viscosity of the formulations. The target viscosity is often established under deposit salinity via variation of the concentration.

D) dependence of the pH of the formulation on the thickening properties or the viscosity (for example in the case of use of carboxylates) is possible.

E) a combination of the derivative of tris(2-hydroxyphenyl) methane with one or more further surfactants is possible F) it is optionally also possible to use further components, such as biocides, in the formulation. In general, biocides are already used for the water treatment. Especially waters of low salinity can be treated with algicides, fungicides, etc.

The examples which follow and the claims are intended to illustrate the invention in detail.

EXAMPLE 1

Synthesis of tris(2-hydroxyphenyl)methane derivatives 1.1 Synthesis of tris(3,5-di-tert-butyl-2-hydroxyphenyl)methane Tris(3,5-di-tert-butyl-2-hydroxyphenyl)methane (CAS No. 143560-44-5) was prepared by means of the process described by M. B. Dinger, M. J. Scott, *Eur. J. Org. Chem.* 2000, 2467. Tris(3,5-di-tert-butyl-2-hydroxyphenyl)methane is also abbreviated to TRIS hereinafter.

1.2 Synthesis of TRIS[(—CH$_2$—CH$_2$—O)$_{11}$H]$_3$ by ethoxylation of TRIS with 33 EO Units In a 2 l autoclave, TRIS (100 g) suspended in toluene (150 ml) is admixed with potassium tert-butoxide (3.0 g). The autoclave is purged three times with N$_2$, a supply pressure of approx. 1.3 bar of N$_2$ is established and the temperature is increased to 119-121° C. Ethylene oxide (231 g) is metered in at such a rate that the temperature remains between 119° C.-130° C. This is followed by stirring at 90° C. for 16 h, purging with N$_2$, cooling to 70° C. and emptying of the reactor. The basic crude product is neutralized with the aid of commercial magnesium silicates, which are subsequently filtered off. The solvent is removed and the product is dried for 5 hours at 80° C. and a pressure of 20 mbar.

This gives 263 g of intermediate having an OH number of 105.9 mg/g. In a second step, 239 g of the intermediate thus obtained are admixed with potassium tert-butoxide (1.5 g) in a 2 l autoclave. The autoclave is purged three times with N$_2$, a supply pressure of approx. 1.3 bar of N$_2$ is established and the temperature is increased to 119-121° C. Ethylene oxide (74 g) is metered in at such a rate that the temperature remains between 119° C.-130° C. This is followed by stirring at 100° C. for 16 h, purging with N$_2$, cooling to 70° C. and emptying of the reactor. The basic crude product is neutralized with the aid of commercial magnesium silicates, which are subsequently filtered off. In this way, 307 g of the target compound are obtained. OH number: 87.5 mg/g. The TAI $^1$H NMR (see J. Loccufier, M. van Bos, E. Schacht, Polymer Bulletin, 1991, 27, 201) of the substance shows a mean ethoxylation level of 11 ethylene oxide units per phenolic OH group.

Alternatively, the product can also be prepared in the presence of [18]crown-6 crown ether as follows:

In a 2 l autoclave, TRIS (80 g) is suspended in toluene (220 ml), and potassium tert-butoxide (2.2 g) and [18]crown-6 crown ether (5.3 g) are added.

The autoclave is purged three times with N$_2$, a supply pressure of approx. 1.3 bar of N$_2$ is established and the temperature is increased to 130° C. Ethylene oxide (185 g) is metered in within 3 h, in the course of which the temperature is kept at 130° C. This is followed by stirring at 130° C. for 8 h and then at 50° C. overnight. Volatile organic compounds are removed by a nitrogen stream and the reactor is emptied. The basic crude product is neutralized with the aid of commercial magnesium silicates, which are subsequently filtered off. The solvent is removed with the aid of a rotary evaporator and the product is subsequently dried at 80° C. and p=20 mbar for 5 h. This gives 277 g of the product. SEC shows $M_n$=2080 g/mol and $M_w$=2136 g/mol, and a polydispersity $M_w/M_n$=1.03. The product is also characterized by means of $^1$H NMR.

1.3 Synthesis of TRIS[(—CH$_2$—CH$_2$—O)$_{11}$H]$_2$[(—CH$_2$—CH$_2$—O)$_{11}$—SO$_3$Na] by sulfonation The TRIS[(—CH$_2$—CH$_2$—O)$_{11}$H]$_3$ product synthesized in Example 1.2 is dissolved in dichloromethane (45 g) and cooled to 5-10° C. Thereafter, chlorosulfonic acid (2.12 g) is added dropwise at such a rate that the temperature does not exceed 10° C. The mixture is left to stir at 10° C. for 1 h, then at room temperature overnight, before the above reaction mixture is added dropwise to an aqueous NaOH solution (50%, 1.98 g) at max. 10° C. The dichloromethane is removed at 30-45° C. on a rotary evaporator under gentle vacuum. The product is characterized by $^1$H NMR and the water content of the solution is determined (approx. 60%).

1.4 Synthesis of TRIS[(—CH$_2$—CH$_2$—O)$_{11}$—SO$_3$Y]$_3$ (Y=Na$^+$, NH$_4^+$) by ethoxylation of TRIS with 33 EO Units and Subsequent Full Sulfonation The product from synthesis example 1.2 (30 g), aminosulfonic acid (CAS 5329-14-6; 5.0 g) and catalytic amounts of urea (17 mg) are heated to 85° C. for 7 h. After cooling to room temperature, 35 g of water are added and the pH of the solution thus obtained is adjusted to pH=9 with 50% sodium hydroxide solution. The product is characterized by means of $^1$H NMR and the water content of the solution is determined (approx. 47%).

1.5 Synthesis of TRIS[(CH$_2$CH(CH$_3$)—O)$_{4.4}$—(—CH$_2$—CH$_2$—O)$_{13}$H]$_3$ by propoxylation of TRIS with 13.2 PO Units and Subsequent ethoxylation with 39 EO Units In a 2 l autoclave, TRIS (50 g) is suspended in toluene (130 ml), and potassium tert-butoxide (1.4 g) and [18]crown-6 crown ether (3.3 g) are added.

The autoclave is purged three times with N$_2$, a supply pressure of approx. 1.3 bar of N$_2$ is established and the temperature is increased to 130° C. Propylene oxide (61 g) is metered in within 80 min, in the course of which the temperature is kept at 130° C. Subsequently, the mixture is stirred at 130° C. for 8 h and then at 50° C. overnight. The next day, the reaction mixture is heated to 130° C. and ethylene oxide (136.4 g) is metered in over a period of 2 h, in the course of which the temperature is kept at 130° C. This is followed by stirring at 130° C. for 8 h and then at 50° C. overnight.

Volatile organic compounds are removed by a nitrogen stream and the reactor is emptied. The basic crude product is neutralized with the aid of commercial magnesium silicates, which are subsequently filtered off. The solvent is removed with the aid of a rotary evaporator and the product is then dried at 80° C. and p=20 mbar for 2 h. This gives 236 g of the product. SEC shows $M_n$=2965 g/mol and $M_w$=3139 g/mol and a polydispersity $M_w/M_n$=1.1. The product is also characterized by means of $^1$H NMR.

1.6 Alkoxylation of TRIS with 24 Glycidol Units and 9 Ethylene Oxide Units

In an autoclave, TRIS (50 g) is suspended in toluene (100 g), and potassium tert-butoxide (1.7 g) and [18]crown-6 crown ether (4 g) are added. The autoclave is purged three times with $N_2$, a supply pressure of approx. 1.3 bar of $N_2$ is established and the temperature is increased to 120° C. A mixture of glycidol (142 g) and ethylene oxide (31.5 g) is metered in over a period of 8 h at such a rate that the temperature remains at 120° C. This is followed by stirring at 80° C. for 16 h, purging with $N_2$, cooling to 70° C. and emptying of the reactor. The basic crude product is neutralized with the aid of commercial magnesium silicates, which are subsequently filtered off. The solvent is removed and the product is dried for 5 hours at 80° C. and a pressure of 20 mbar. 200 g of the target product are obtained. The product is characterized by means of $^1$H NMR.

1.7 Synthesis of TRIS[($CH_2CH_2$—O)$_8$—(—$CH_2$—CH($CH_2OH$)—O)$_3$H]$_3$

Stoichiometry:TRIS:ethylene oxide:benzyl glycidyl ether=1:24:9

In a 2 l autoclave, TRIS (50 g) is suspended in toluene (130 ml), and potassium tert-butoxide (1.4 g) and [18]crown-6 crown ether (3.3 g) are added. The autoclave is purged three times with $N_2$, a supply pressure of approx. 1.3 bar of $N_2$ is established and the temperature is increased to 130° C. Ethylene oxide (84 g) is metered in within 2 h, in the course of which the temperature is kept at 130° C. This is followed by stirring at 130° C. for 5 h and then at 40° C. overnight.

The next day, the reaction mixture is heated to 120° C., and benzyl glycidyl ether (CAS. 2930-05-4; 117 g) is metered in over a period of 2 h, in the course of which the temperature is kept at 120° C.

This is followed by stirring at 120° C. for 5 h and then at 40° C. overnight. Volatile organic compounds are removed by a nitrogen stream and the reactor is emptied.

The basic crude product is neutralized with the aid of commercial magnesium silicates, which are subsequently filtered off. The solvent is removed with the aid of a rotary evaporator and the product is then dried at 80° C. and p=20 mbar for 3 h. This gives 240 g of the benzyl-protected intermediate. The intermediate thus obtained (200 g) is dissolved in a mixture of ethyl acetate (500 ml) and $H_2O$ (500 ml), palladium on activated carbon (10%, 20 g) is added and the mixture is transferred into a 2.5 l autoclave. The autoclave is inertized three times with $N_2$ and then hydrogen is metered in up to a pressure of 10 bar. Subsequently, the reactor contents are heated to 80° C. and this reaction temperature is maintained for 20 h, in the course of which the hydrogen pressure is kept at 10 bar. The reactor is cooled to room temperature, decompressed, inertized three times with $N_2$ and emptied.

The heterogeneous catalyst is filtered off by means of a suction filter under $N_2$, and organic solvents are removed on a rotary evaporator under reduced pressure at 80° C.

This gives 396.5 g of the product which, according to Karl Fischer titration, comprises 65.8% water. For analytical purposes, the water is removed azeotropically with toluene in a small sample. SEC (THF+0.1% trifluoroacetic acid as eluent) shows Mn=2090 g/mol and Mw=2440 g/mol and a polydispersity Mw/Mn=1.2.

The product is also characterized unambiguously by means of $^1$H NMR.

1.8 Synthesis of TRIS[($CH_2CH_2$—O)$_8$—(—$CH_2$—CH($CH_2OH$)—O)$_2$H]$_3$

The compound was prepared analogously to example 1.7 by varying the stoichiometry (TRIS:ethylene oxide:benzyl glycidyl ether=1:24:6).

1.9 Synthesis of TRIS[($CH_2CH_2$—O)$_{11}$—(—$CH_2$—CH($CH_2OH$)—O)$_1$H]$_3$ The compound was prepared analogously to example 1.7 by varying the stoichiometry (TRIS:ethylene oxide:benzyl glycidyl ether=1:33:3).

1.10 Synthesis of TRIS[($CH_2CH_2$—O)$_7$—(—$CH_2$—CH($CH_2OH$)—O)$_4$H]$_3$ The compound was prepared analogously to example 1.7 by varying the stoichiometry (TRIS:ethylene oxide:benzyl glycidyl ether=1:21:12).

1.11 Synthesis of TRIS[($CH_2CH_2$—O)$_6$—(—$CH_2$—CH($CH_2OH$)—O)$_4$H]$_3$ The compound was prepared analogously to example 1.7 by varying the stoichiometry (TRIS:ethylene oxide:benzyl glycidyl ether=1:18:12).

1.12 Synthesis of TRIS[($CH_2CH_2$—O)$_5$—(—$CH_2$—CH($CH_2OH$)—O)$_5$H]$_3$ The compound was prepared analogously to example 1.7 by varying the stoichiometry (TRIS:ethylene oxide:benzyl glycidyl ether=1:15:15).

1.13 Synthesis of TRIS[($CH_2CH_2$—O)$_{10}$]$_3$

In a 2 l autoclave, TRIS (50 g) is suspended in toluene (130 ml), and potassium tort-butoxide (1.4 g) and [18]crown-6 crown ether (3.3 g) are added. The autoclave is purged three times with $N_2$, a supply pressure of approx. 1.3 bar of $N_2$ is established and the temperature is increased to 130° C. Ethylene oxide (105 g) is metered in within 2 h, in the course of which the temperature is kept at 130° C. This is followed by stirring at 130° C. for 5 h and then at 40° C. overnight. Volatile organic compounds are removed by a nitrogen stream and the reactor is emptied. The basic crude product is neutralized with the aid of commercial magnesium silicates, which are subsequently filtered off. The solvent is removed with the aid of a rotary evaporator and the product is then dried at 80° C. and p=20 mbar for 3 h. This gives 155 g of the product with an OH number of 89.2 mg KOH/g. The product is also characterized by means of $^1$H NMR.

1.14 Synthesis of TRIS[($CH_2CH_2$—O)$_9$—(—$CH_2$COONa)]$_3$

A mixture of the product from synthesis example 1.13 (92.2 g) and Raney copper (18.44 g, water-moist, dry content approx. 12 g) is heated to 200° C. At this temperature, sodium hydroxide solution (5%, 117.48 g) is metered in over a period of 6 h, in the course of which water and hydrogen escape continuously from the reaction mixture. After the addition has ended, the reaction mixture is stirred at 200° C. for 0.5 h and then cooled to room temperature. The reaction mixture is taken up in water and the heterogeneous catalyst is filtered off. Subsequently, the filtrate is concentrated with the aid of a rotary evaporator. The product is characterized by means of $^1$H NMR and the water content is determined by means of Karl Fischer titration (3.6%).

1.15 Synthesis of TRIS[($CH_2CH_2$—O)$_9$]$_3$

In a 0.3 l autoclave, TRIS (25.2 g) is suspended in toluene (46.4 g), and potassium tert-butoxide (0.84 g) is added.
The autoclave is purged three times with $N_2$, a supply pressure of approx. 1.3 bar of $N_2$ is established and the temperature is increased to 130° C. Ethylene oxide (47.52 g) is metered in, in the course of which the temperature is kept at 130° C. This is followed by stirring at 130° C. overnight. The mixture is cooled to 40° C., volatile organic compounds are removed with a nitrogen stream, and the reactor is emptied. The basic crude product is neutralized with the aid of commercial magnesium silicates, which are subsequently filtered off. The solvent is removed with the aid of a rotary evaporator and the product is subsequently dried at 80° C. and p=20 mbar for 3 h. This gives 118 g of the product with an OH number of 100.2 mg KOH/g. The product is also characterized by means of $^1$H NMR.

1.16 Synthesis of TRIS[($CH_2CH_2$—O)$_9$]$_3$

Sulfonation Level 50%

The product from synthesis example 1.15 (50 g), amino sulfonic acid (CAS 5329-14-6; 9.1 g) and catalytic amounts of urea (32 mg) are heated to 85° C. for 7 h, in the course of which a light brown mass forms.
After cooling to room temperature, 40 g of water are added and the reaction mixture is heated to 80° C. The pH of the solution thus obtained is adjusted to pH=9 with 50% sodium hydroxide solution (5.6 g). By $^1$H NMR, the sulfonation level is determined (50%). The water content of the solution is determined by Karl Fischer titration (41.5%).

1.17 Synthesis of TRIS[($CH_2CH_2$—O)$_6$]$_3$

Analogously to synthesis example 1.13, TRIS (100 g) is reacted with ethylene oxide (126 g). This gives 223 g of the product.

1.18 Synthesis of TRIS[($CH_2CH_2$—O)$_6$-glycoside]$_3$

A mixture of the product from synthesis example 1.17 (11.3 g), acetobromo-α-D-glucose (13.1 g; CAS 572-09-8, from Aldrich), potassium carbonate (5.45 g), benzyltributylammonium chloride (0.49 g) and chloroform (30 ml) is stirred at room temperature for 21 h. Subsequently, solid constituents are filtered off and the solids are washed with chloroform (20 ml). The filtrate is concentrated with the aid of a rotary evaporator. This gives 23.7 g of the acetyl-protected intermediate. For deprotection, the intermediate (8.0 g) is dissolved in methanol (100 ml), and a solution of NaOMe in MeOH (30%, 1.8 g) is added. The solution thus obtained is stirred at room temperature overnight, before the acidic ion exchanger Amberlite IRC86 (from Fluka, 10 g) is added.
The ion exchanger is subsequently filtered off and the filtrate is concentrated with the aid of a rotary evaporator. The product is obtained in the form of a dark mass. MALDI-MS confirms the glycosylation.

EXAMPLE 2

Physicochemical studies

Figure 2:
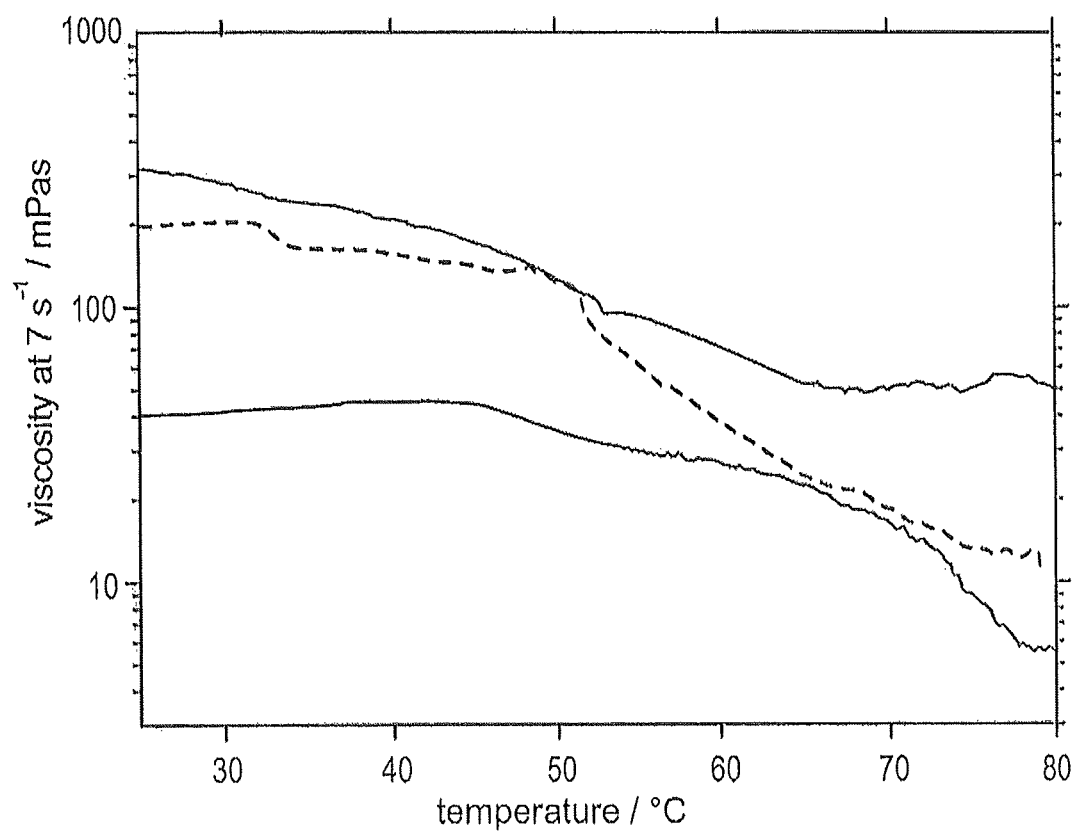
Figure 3:
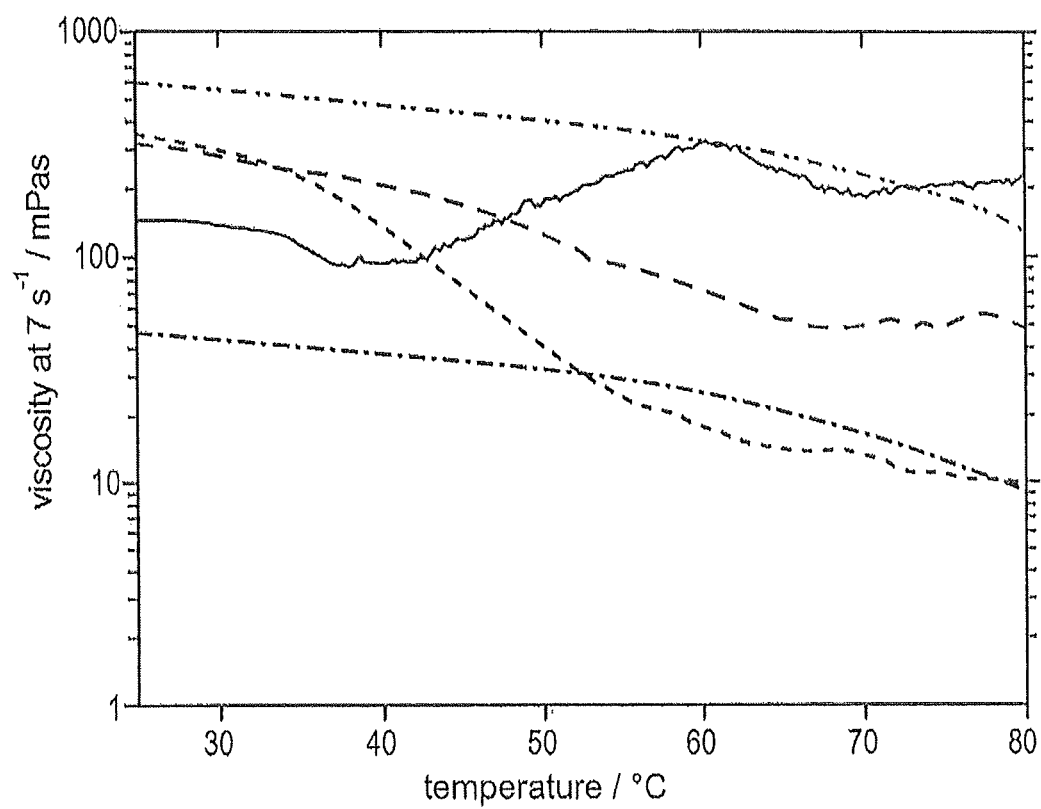

Viscosity
The viscosity measurements were conducted with a rheometer (Anton Paar MCR 301). For the viscosity measurements, aqueous solutions of the components were used.
To dissolve the inventive tris(2-hydroxyphenyl)methane derivatives, the following aqueous media were used:
Demineralized Water
Deposit water from the Bockstedt mineral oil deposit in Northern Germany (synthetic):
  Total salinity: 185 548 mg/l
  $Na^+$ 52079 mg/l, $Mg^{2+}$ 2681 mg/l, $Ca^{2+}$ 15383 mg/l, $Cl^-$ 115105 mg/l, borate 117 mg/l, $SO_4^{2-}$ 183 mg/l; ratio of alkali metal ions/alkaline earth metal ions: 2.9; deposit water with high $Ca^{2+}$ content.
Unless stated otherwise, the weight figures are based on the proportion by mass in percent by weight.
Analysis of TRIS[(—$CH_2$—$CH_2$—O)$_{11}$H]$_3$ and the various tris(2-hydroxyphenyl)methane derivatives
Thickening Properties
The studies which follow show the thickening properties of the inventive structures in salt-free solution and under high-salinity conditions, and over a broad temperature range. The results show that the thickening properties of the inventive compounds are robust with respect to salinity and temperature (FIGS. 1-4).
FIG. 1 shows the general shear profile of the inventive synthesis examples. For 0.25% by weight solutions of TRIS [(—$CH_2$—$CH_2$—O)$_{11}$H]$_3$ (synthesis example 1.2) at 25° C., it can be seen that the thickening action (viscosity) is maintained under practice-relevant shear conditions not only in salt-free solution (lower curve) but also under high-salinity conditions (upper curve:deposit water).
FIG. 2 shows the temperature-dependent thickening (viscosity) from 25 to 80° C. under high-salinity conditions (deposit water) for three different tris(2-hydroxyphenyl)methane derivatives (each 1% solutions) at a constant shear rate of 7 s$^{-1}$:
  a) TRIS[(—$CH_2$—$CH_2$—O)$_{11}$—$SO_3$Y]$_3$ (synthesis example 1.4; lower curve)
  b) TRIS[($CH_2CH_2$—O)$_9$—(—$CH_2$COONa)]$_3$ (synthesis example 1.14; upper curve)
  c) TRIS[($CH_2CH_2$—O)$_9$]$_3$, sulfonation level 50% (synthesis example 1.16; middle curve).
FIG. 3 shows the temperature-dependent thickening (viscosity) from 25 to 80° C. under high-salinity conditions (Bockstedt water) for two different tris(2-hydroxyphenyl) methane derivatives (each 1% solutions) compared to three known thickener components: the polymeric thickeners Floopaam 3630S (from SNF) and Alcoflood 1285 Red (from BASF), and the quaternary ammonium salt cetyltrimethylammonium tosylate (CTAT, CAS 138-32-9; from Aldrich):
a) TRIS[($CH_2CH_2$—O)$_9$—(—$CH_2$COONa]$_3$ (synthesis example 1.14 (1%) ( - - - line))
b) Flopaam 3630S (1%) (lowermost line, _._._._._._._.)
c) Alcoflood 1285 Red (1%) (uppermost line, _.._.._.._._.._.._.._._.)
d) CTAT ( . . . line)
e) TRIS[($CH_2CH_2$—O)$_{11}$—(—$CH_2$—CH($CH_2$OH)—O)$_1$H]$_3$ (synthesis example 1.9) (1%) (continuous line).

Figure 4:
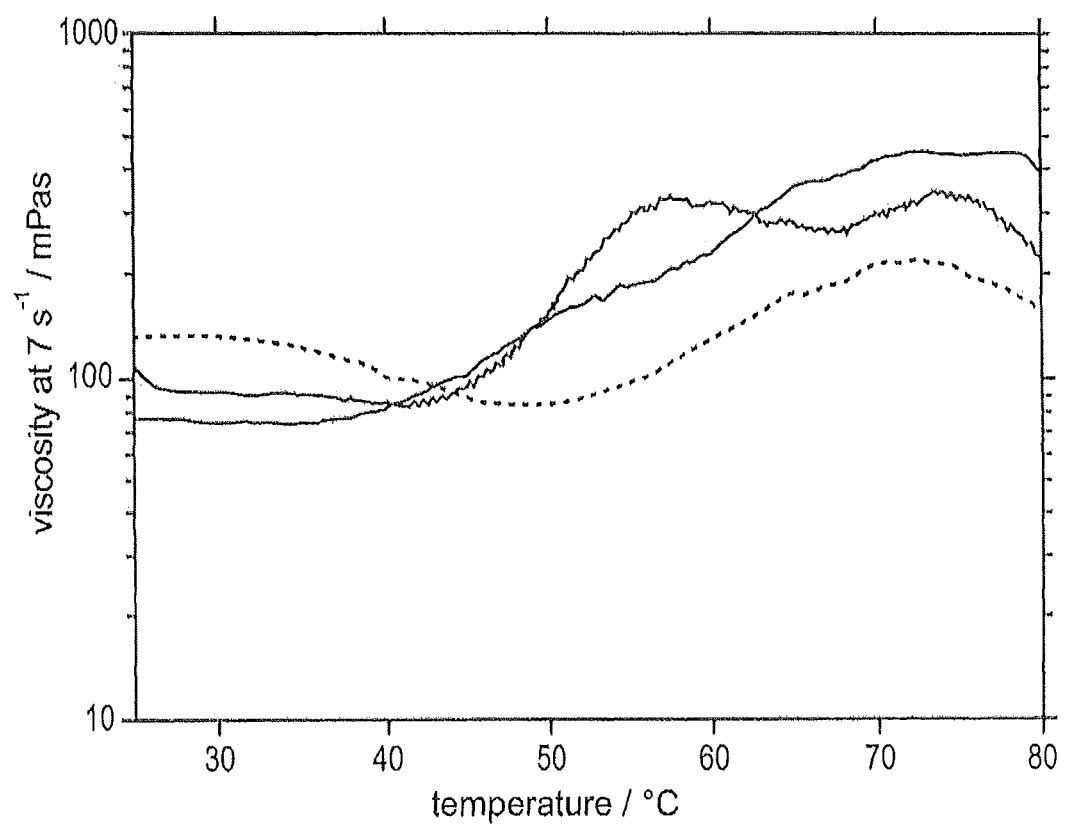

FIG. 4 shows the temperature-dependent thickening (viscosity) from 25 to 80° C. at a constant shear rate of 7 s$^{-1}$ under high-salinity conditions (deposit water) for three different tris(2-hydroxyphenyl)methane derivatives (each 1% solutions):
a) TRIS[($CH_2CH_2$—O)$_{11}$—(—$CH_2$—CH($CH_2$OH)—O)$_1$H]$_3$ (synthesis example 1.9) (1%) ( . . . line)
b) TRIS[($CH_2CH_2$—O)$_8$—(—$CH_2$—CH($CH_2$OH)—O)$_2$H]$_3$ (synthesis example 1.8)(1%) (continuous line)
c) TRIS[($CH_2CH_2$—O)$_8$—(—$CH_2$—CH($CH_2$OH)—O)$_3$H]$_3$ (synthesis example 1.7) (1%) ( - - - line).

Figure 5:
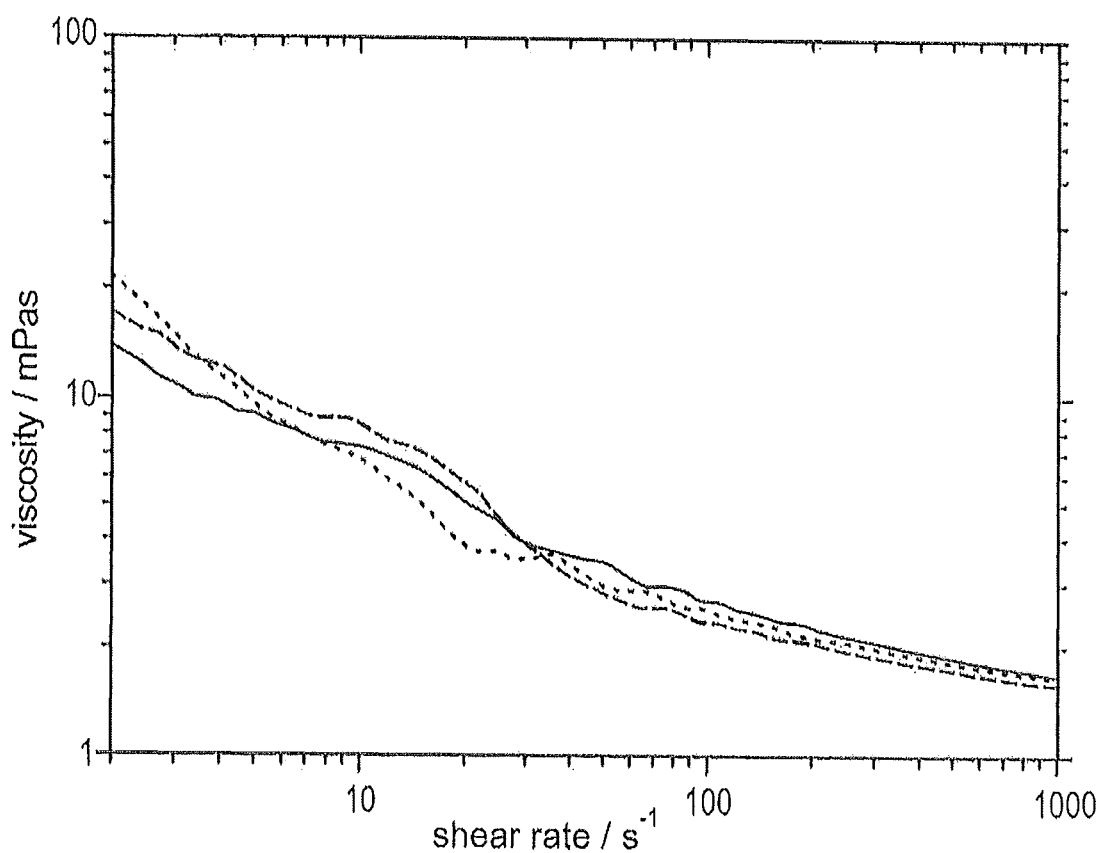

FIG. 5 shows the stability of the micellar systems comprising TRIS[(—$CH_2$—$CH_2$—O)$_{11}$H]$_3$ (synthesis example 1.2) in salt-containing water (93 g of salt/liter; corresponds to 50% salinity of the deposit water), water (0.1% solution of the thickener) with respect to crude oil. The viscosities were determined at 25° C.:
a) No contact with the crude oil (continuous line)
b) 15 days after contact with the crude oil (at 50° C.) ( - - - line)
c) 50 days after contact with the crude oil (at 25° C.) ( . . . line).

The measurements show that the viscosity of the aqueous solutions of TRIS[(—$CH_2$—$CH_2$—O)$_{11}$H]$_3$ (synthesis example 1.2) does not change after contact with crude oil. This is not observed in the case of the known viscoelastic solutions of ionic or betaine surfactants which have alkyl chains as the hydrophobic moiety (e.g. cetylpyridinium salicylate).

Viscoelastic Properties:

In oscillatory shear experiments, the viscoelastic properties of a liquid can be determined. The storage modulus G' characterizes the elastic properties of a material, the loss modulus G" the viscous properties. The results are shown in FIG. 6.

Figure 6:
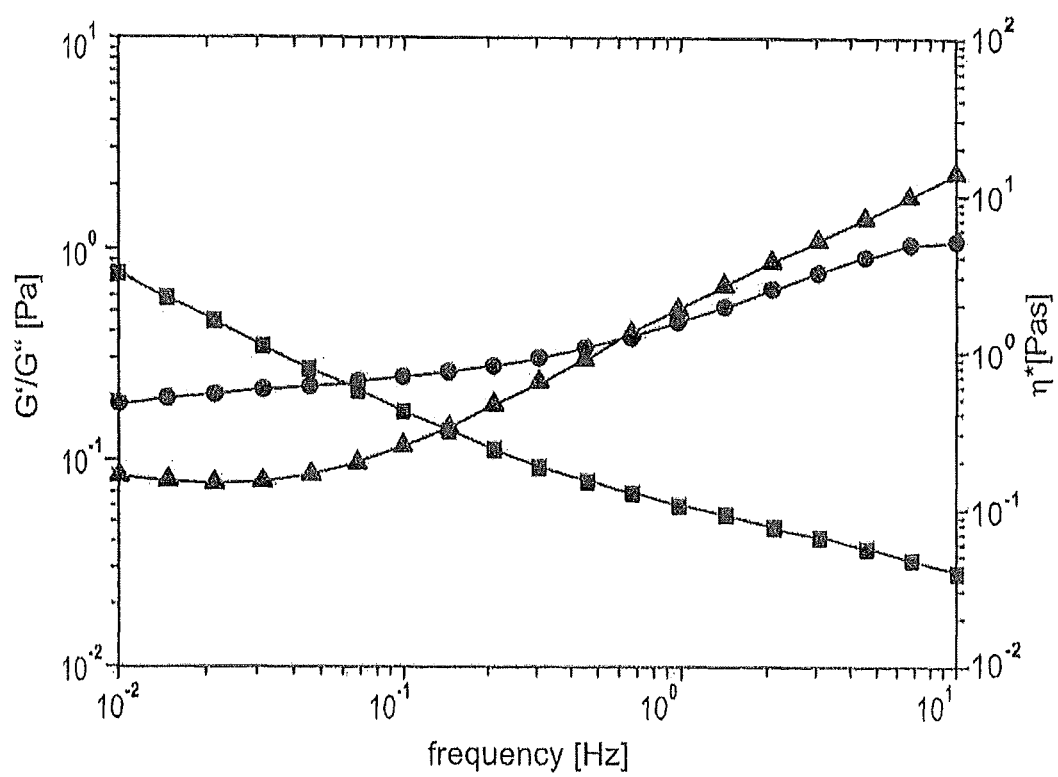

FIG. 6 shows the properties (in Pa or Pas):
Storage modulus G' (-●-),
Loss modulus G" (-▲-) and
Complex viscosity η* (-■-)
of a 0.25% solution in deposit water of TRIS[(—$CH_2$—$CH_2$—O)$_{11}$H]$_3$
(synthesis example 1.2) as a function of frequency (in Hz) at constant deformation of 10%.

Interfacial Activity:

By means of the known Du Nouy ring method (DIN EN 14210), a standard tensiometer was used to determine the surface tension of the surfactant in aqueous solution (demineralized water). The plot of surface tension as a function of surfactant concentration was used to determine the critical micelle formation concentration (cmc).

For TRIS[(—$CH_2$—$CH_2$—O)$_{11}$H]$_3$ (synthesis example 1.2), the surface tension is 32 mN/m (1 g/l, 25° C.). The critical micelle formation concentration in demineralized water is 0.03 g/l (25° C.).

The pendant drop and spinning drop methods were used to determine the interfacial tension of an aqueous surfactant solution with respect to hexadecane as the oil phase. The table shows the interfacial tensions (mN/m) of 0.5% solutions of TRIS[(—$CH_2$—$CH_2$—O)$_{11}$H]$_3$ (synthesis example 1.2) in salt-containing water (93 g of salt/liter; corresponds to the 50% salinity of the deposit water) with respect to crude oil from the Emlichheim deposit, measured under the conditions specified.

The interfacial tension of the salt-containing water with respect to crude oil without additives is 14 mN/m at 23° C. and 13 mN/m at 60° C.

| Method | 23° C. | 60° C. |
|---|---|---|
| Pendant drop (1 h) | 2.21 | 0.73 |
| Spinning drop (1 h) | 2.3 | 1.4 |

The measurements show that TRIS[(—$CH_2$—$CH_2$—O)$_{11}$H]$_3$ (synthesis example 1.2) lowers the interfacial tension between crude oil and salt-containing water, which in turn facilitates the mobilization of the oil.

EXAMPLE 3

Production of a Formulation for EOR

The above-described inventive triphenoxymethane derivatives are particularly suitable for deposits with extreme salinities (tests have been conducted up to salt content of approx. 200 g/l of TDS) at moderately elevated temperatures up to 80° C. A reduction in the salinity makes much higher temperature ranges accessible. TriX is of particular suitability for $Ca^{2+}$/$Mg^{2+}$-containing deposits.

As a viscoelastic surfactant system, TriX has significant shear dilution and can therefore be pumped particularly efficiently in the inventive compositions. There is no observation of degradation resulting from high shear. The possibility of rapid pumping is a further advantage over polymer solutions. No chemical degradation is observed.

The invention claimed is:
1. An aqueous formulation comprising, as components:
0.001 to 99% by weight of at least one tris(2-hydroxyphenyl)methane derivative of the formula (I):

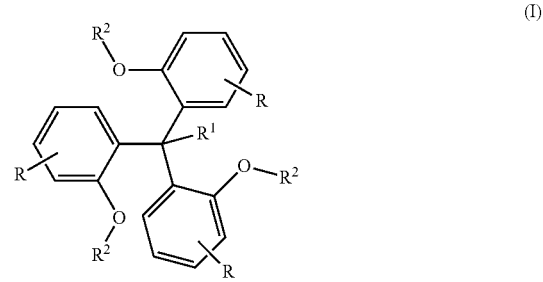

where the $R^1$, $R^2$ and R radicals in the formula (I) are each defined as follows:
R is in each case independently 0 to 4
$C_1$- to $C_{30}$-hydrocarbyl radicals per phenyl ring,
$R^1$ is a radical selected from the group of H, OH, F, Cl, Br, I and $C_1$- to $C_{30}$-hydrocarbyl groups,
$R^2$ are each independently radicals of the general formula (III),

—($R^5$—O—)$_n$—$R^6$—X        (III)

where n is a number from 1 to 50, and
where the $R^5$ radicals are each independently selected from the group of $R^7$, $R^8$ and $R^9$ radicals

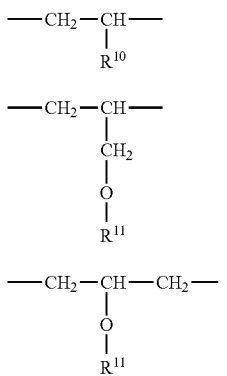

where $R^6$, X, $R^{10}$ and $R^{11}$ are each independently defined as follows:
- $R^6$ is a single bond or an alkylene group having 1 to 10 carbon atoms, which may optionally have functional groups as substituents,
- X is H or a hydrophilic group,
- $R^{10}$ is H or a $C_1$ to $C_6$-hydrocarbyl radical,
- $R^{11}$ is a —$(R^5$—O—$)_m$—$R^6$—X group,
- where m is a number from 0 to 50, and where the total number z of all $R^5$ groups in one $R^2$ radical is 1 to 50, with the proviso that z is a number from 2 to 50 if at least one X is H;

10 000 ppm to 350 000 ppm of inorganic salt, 0.01 to 5% by weight of at least one further auxiliary component for mineral oil production selected from the group consisting of surfactants, antioxidants, biocides, and combinations thereof, water, and optionally further solvents.

2. The aqueous formulation according to claim 1, comprising:
0.1 to 90% by weight of a tris(2-hydroxyphenyl)methane derivative of the formula (II):

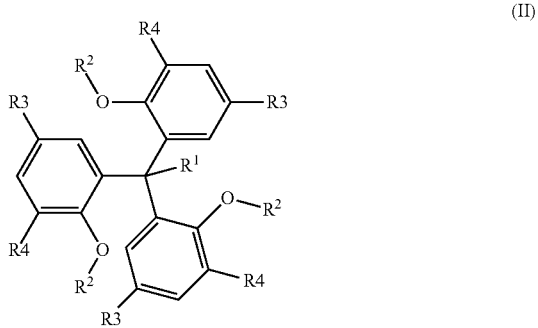

(II)

where $R^1$ and $R^2$ are each as defined in claim 1 and $R^3$ and $R^4$ are each independently H or a $C_1$ to $C_{30}$-hydrocarbyl radical,
50 000 ppm to 350 000 ppm of inorganic salt,
0.01 to 5% by weight of at least one auxiliary component selected from the group consisting of surfactants, antioxidants, biocides, and combinations thereof,
water, and
optionally further solvents.

3. The aqueous formulation according to claim 1, comprising:
0.1 to 90% by weight of a tris(2-hydroxyphenyl)methane derivative selected from the group consisting of
TRIS[(—$CH_2$—$CH_2$—O$)_{11}$H$]_3$
TRIS[(—$CH_2$—$CH_2$—O$)_{11}$H$]_2$[(—$CH_2$—$CH_2$—O$)_{11}$—$SO_3$Na]
TRIS[(—$CH_2$—$CH_2$—O$)_{11}$—$SO_3$Y$]_3$ (Y=$Na^+$, $NH_4^+$)
TRIS[($CH_2CH(CH_3)$—O$)_{4,4}$—(—$CH_2$—$CH_2$—O$)_{13}$H$]_3$
TRIS with 24 glycidol units and 9 EO units
TRIS[($CH_2CH_2$—O$)_8$—(—$CH_2$—CH($CH_2OH$)—O$)_3$H$]_3$
TRIS[($CH_2CH_2$—O$)_8$—(—$CH_2$—CH($CH_2OH$)—O$)_2$H$]_3$
TRIS[($CH_2CH_2$—O$)_{11}$—(—$CH_2$—CH($CH_2OH$)—O$)_1$H$]_3$
TRIS[($CH_2CH_2$—O$)_7$—(—$CH_2$—CH($CH_2OH$)—O$)_4$H$]_3$
TRIS[($CH_2CH_2$—O$)_6$—(—$CH_2$—CH($CH_2OH$)—O$)_4$H$]_3$
TRIS[($CH_2CH_2$—O$)_5$—(—$CH_2$—CH($CH_2OH$)—O$)_5$H$]_3$
TRIS[($CH_2CH_2$—O$)_{10}]_3$
TRIS[($CH_2CH_2$—O$)_9$—(—$CH_2COONa$)$]_3$ where TRIS represents tris(3,5-di-tert-butyl-2-hydroxyphenyl)methane,
50 000 ppm to 350 000 ppm of inorganic salt,
0.01 to 5% by weight of at least one auxiliary component selected from the group consisting of surfactants, antioxidants, biocides, and combinations thereof,
water, and
optionally further solvents.

4. The aqueous formulation according to claim 1, wherein R is in each case 1 to 2.

5. The aqueous formulation according to claim 1, wherein $R^1$ is H or OH.

6. The aqueous formulation according to claim 1 wherein $R^5$ radicals are selected from the group of $R^7$ and $R^8$.

7. The aqueous formulation according to claim 1 wherein the total number z of all $R^5$ groups in one $R^2$ radical is 8 to 35.

8. A process for mineral oil production, comprising injecting the aqueous formulation according to claim 1 into a mineral oil deposit through at least one injection well and withdrawing crude oil from the deposit through at least one production well.

9. The process for mineral oil production according to claim 8, wherein the at least one derivative of tris(2-hydroxyphenyl)methane is of the general formula (II)

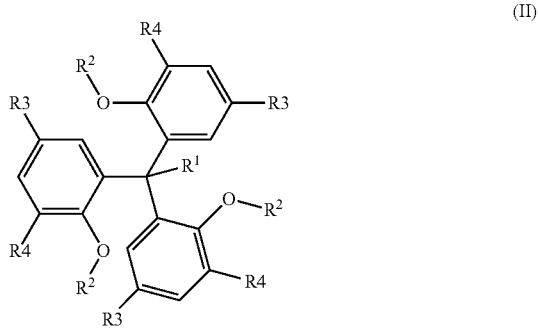

(II)

where $R^3$ and $R^4$ are each independently H or a $C_1$ to $C_{30}$-hydrocarbyl radical.

10. The process according to claim 9, wherein the compound of the formula (II) used is one in which all $R^3$ and $R^4$ are independently straight-chain or branched $C_1$-to $C_6$-hydrocarbyl radicals.

11. The process according to claim 8, wherein each X is an acid group selected from carboxyl groups —COOM, sulfo groups —$SO_3M$, sulfate groups —$OSO_3M$, phosphonic acid groups —$PO_2M_2$ or phosphoric acid groups —$OPO_3M_2$, where M is $H^+$ or a k-valent counterion $1/kY^{k+}$, especially Na, K or ammonium ions.

12. The process according to claim 8, wherein each X is an acidic group selected from carboxyl groups —COOM, sulfa groups —$SO_3M$ or sulfate groups —$OSO_3M$, where M is $H^+$ or an alkali metal or alkaline earth metal counterion.

13. The process according to claim 8, wherein the $R^5$ radicals are $R^7$ and/or $R^8$ groups.

14. The process according to claim 8, wherein the derivatives of tris(2-hydroxyphenyl)-methane used have a mean molar mass of 2000 to 3000 g/mol and the three 2-hydroxyphenyl groups are of the same structure.

15. The process according to claim 8, wherein the temperature of the mineral oil deposit is 10 to 150° C.

16. The process according to claim 8, wherein the mineral oil production is effected from deposits with a deposit temperature of 10 to 150° C., said deposit comprising, as well as mineral oil, also deposit water with a salinity of 20 000 ppm to 350 000 ppm and the mineral oil having a viscosity measured at deposit temperature of at least 3 mPa*s, by injecting the aqueous formulation into the mineral oil deposit through at least one injection well and withdrawing crude oil from the deposit through at least one production well, said process comprising:
    providing the at least one tris(2-hydroxyphenyl)methane derivative of the general formula (I) as a concentrate;
    preparing the aqueous formulation by diluting the concentrate provided in step (1) on site with water to a concentration of 0.01 g/l to 10 g/l,
    injecting the aqueous formulation into the mineral oil formation, and
    withdrawing crude oil through at least one production well.

17. The process according to claim 8, wherein the derivative of tris(2-hydroxyphenyl)-methane is an unbranched derivative and the concentration of the tris(2-hydroxyphenyl) methane derivative in the formulation is 0.01 g/l to 5 g/l.

* * * * *